US008158656B2

(12) United States Patent
Lu et al.

(10) Patent No.: US 8,158,656 B2
(45) Date of Patent: Apr. 17, 2012

(54) 2-INDOLINONE DERIVATIVES AS MULTI-TARGET PROTEIN KINASE INHIBITORS AND HISTONE DEACETYLASE INHIBITORS

(75) Inventors: Xian-Ping Lu, Belle Meade, NJ (US); Zhi-Bin Li, Shenzhen (CN); Zhi-Qiang Ning, Shenzhen (CN)

(73) Assignee: Shenzhen Chipscreen Biosciences Ltd., Shenzhen (CN)

( * ) Notice: Subject to any disclaimer, the term of this patent is extended or adjusted under 35 U.S.C. 154(b) by 223 days.

(21) Appl. No.: 12/463,107

(22) Filed: May 8, 2009

(65) Prior Publication Data
US 2009/0298886 A1 Dec. 3, 2009

Related U.S. Application Data

(60) Provisional application No. 61/053,937, filed on May 16, 2008.

(51) Int. Cl.
*A61K 31/4439* (2006.01)
*C07D 401/14* (2006.01)
(52) U.S. Cl. ........................................ 514/339; 546/339
(58) Field of Classification Search ................ 546/277.7; 514/339
See application file for complete search history.

(56) References Cited

U.S. PATENT DOCUMENTS

| 7,041,687 | B2 | 5/2006 | Binch et al. |
| 7,098,330 | B2 | 8/2006 | Bebbington et al. |
| 7,115,739 | B2 | 10/2006 | Bebbington et al. |
| 7,125,905 | B2 | 10/2006 | Tang et al. |
| 7,132,533 | B2 | 11/2006 | Benedict et al. |
| 7,151,096 | B2 | 12/2006 | Ren et al. |
| 7,157,476 | B2 | 1/2007 | Come et al. |
| 7,166,597 | B2 | 1/2007 | Alberti et al. |
| 7,179,910 | B2 | 2/2007 | Guan et al. |
| 7,189,721 | B2 | 3/2007 | Tang et al. |
| 7,214,700 | B2 | 5/2007 | Wei et al. |
| 2002/0103192 | A1 | 8/2002 | Curtin et al. |

FOREIGN PATENT DOCUMENTS

| EP | 0847992 A1 | 6/1998 |
| WO | WO0118171 A2 | 3/2001 |
| WO | WO0170675 A2 | 9/2001 |
| WO | WO0226696 A1 | 4/2002 |

OTHER PUBLICATIONS

Colussi et al., "Histone deacetylase, etc.," Pharmacological Research 62 (2010) 3-10.*
Mund et al., "Epigenetic cancer, etc.," Bioessays 32: 949-957, 2010.*
Manzo et al., :Histone acetyransferase, etc., Expert Opin. Ther. Patents (2009) 19(5), 761-774.*
Lodish et al., "Endocrine side, etc.," Endocrine-Related Cancer (2010) 17, R233-R244.*
Batty et al., "Histone deacetylase, etc.," Cancer Letter 280 (2009) 192-200.*
Ouaissi et al., "Rationale for Possible, etc.," Journal of Biomedicine and Biotechnology, 2011, Article: ID 315939, 1-8.*
Dietz et al., "HDAC inhibitors, etc.," Pharmacological Research 62 (2010) 11-17.*
Tan, S-L. et al., "Resistance to Experimental Autoimmune Encephalomyelitis and Impaired IL-17 Production in Protein Kinase Cθ-Deficient Mice", The Journal of Immunology, 2006, vol. 176, pp. 2872-2879.
Healy, A. M., et al., "PKC-δ-Deficient Mice Are Protected from Th1-Dependent Antigen-Induced Arthritis", The Journal of Immunology, 2006, vol. 177, pp. 1886-1893.
Salek-Ardakani, S. et al., "Protein Kinase Cθ Controls Th1 Cells in Experimental Autoimmune Encephalomyelitis", The Journal of Immunology, 2005, vol. 175, pp. 7635-7641.
Kim, J. et al., "PKC-δ Knockout Mice are Protected from Fat-induced Insulin Resistance", The Journal of Clinical Investigation, 2004, vol. 114, No. 6, 823-827.
Arteaga, C. L. et al, "Tyrosine Kinase Inhibitors-ZD1839 (Iressa)", Current Opinion in Oncology, (2001), vol. 13, No. 6, pp. 491-498.
Viloria Petit, A-M. et al., "Neutralizing Antibodies against Epidermal Growth Factor and ErbB-2/neu Receptor Tyrosine Kinases Down-Regulate Vascular Endothelial Growth Factor Production by Tumor Cells in Vitro and in Vivo", American Journal of Pathology, (1997), vol. 5, No. 6, pp. 1523-1530.
Wikstrand, C. L. et al., "Prognostic Applications of the Epidermal Growth Factor Receptor and Its Ligand, Transforming Growth Factor-α", Journal of the National Cancer Institute, 1998, vol. 90, No. 11, pp. 799-801.
Mendelsohn, J., "Epidermal Growth Factor Receptor Inhibition by a Monoclonal Antibody as Anticancer Therapy", Clinical Cancer Research, 1997, vol. 3, pp. 2703-2707.
Rarikh, A. A. et al., "The Vascular Endothelial Growth Factor Family and Its Receptors", Hematology/Oncology Clinics of North America, (2004), vol. 18, pp. 951-971.
Haq, S. et al., "Glycogen Synthase Kinase-3β Is a Negative Regulator of Cardiomyocyte Hypertrophy", The Journal of Cell Biology, 2000, vol. 151, No. 1, pp. 117-129.
Schumacher, J. M. et al., "Air-2: An Aurora/Ipl1-related Protein Kinase Associated with Chromosomes and Midbody Microtubules Is Required for Polar Body Extrusion and Cytokinesis in *Caenorhabditis elegans* Embryos", The Journal of Cell Biology, 1998, vol. 143, No. 6, pp. 1635-1646.
Kimura, M. et al., "Cell Cycle-dependent Expression and Spindle Pole Localization of a Novel Human Protein Kinase, Aik, Related to Aurora of Drosophila and Yeast Ipl1", The Journal of Biological Chemistry, 1997, vol. 272, No. 21, pp. 13766-13771.
Monia, et al. "Antitumor Activity of a Phosphorothioate Antisense Oligodeoxynucleotide Targeted Against C-raf Kinase", Nature Medicine, (1996), vol. 2, No. 6, pp. 668-675.
Grunstein, M., "Histone Acetylation in Chromatin Structure and Transcription", Nature, (1997), vol. 389, pp. 349-352.

(Continued)

*Primary Examiner* — Patricia Morris
(74) *Attorney, Agent, or Firm* — Eckert Seamans Cherin & Mellott, LLC

(57) ABSTRACT

The present invention relates to 2-indolinone derivatives which are capable of inhibiting protein kinases and histone deacetylases. The compounds of this invention are therefore useful in treating diseases associated with abnormal protein kinase activities or abnormal histone deacetylase activities. Pharmaceutical compositions comprising these compounds, methods of treating diseases utilizing pharmaceutical compositions comprising these compounds, and methods of preparing these compounds are also disclosed.

12 Claims, No Drawings

OTHER PUBLICATIONS de Ruijter, A. J. M., et al, "Histone Deacetylases (HDACs): Characterization of the Classical HDAC Family", Biochemical Journal, 2003, vol. 370, pp. 737-749.

Grignani, F. et al., "Fusion Proteins of the Retinoic Acid Receptor-α Recruit Histone Deacetylase in Promyelocytic Leukaemia", Nature, (1998), vol. 391, pp. 815-818.

Lin, R. J. et al., "Role of the Histone Deacetylase Complex in Acute Promyelocytic Leukaemia", Nature, (1998), vol. 391, pp. 811-814.

Marks, P-A., et al., "Histone Deacetylases and Cancer: Causes and Therapies", Nature Reviews Cancer, 2001, vol. 1, pp. 194-202.

Dokmanovic, M. et al. "Prospects: Histone Deacetylase Inhibitors", Journal of Cellular Biochemistry, 2005, vol. 96, pp. 293-304.

Glaser, K. B. et al., "Role of Class I and Class II Histone Deacetylases in Carcinoma Cells Using siRNA", Biochemical and Biophysical Research Communications, (2003), vol. 310, No. 2, pp. 529-536.

Lagger, G. et al., "Essential Function of Histone Deacetylase 1 in Proliferation Control and CDK Inhibitor Repression", The EMBO Journal, 2002, vol. 21, No. 11, pp. 2672-2681.

Bartl, S. et al., "Identification of Mouse Histone Deacetylase 1 as a Growth Factor-Inducible Gene", Molecular and Cellular Biology, 1997, vol. 17, No. 9, pp. 5033-5043.

Trivedi, C. M. et al., "Hdac2 Regulates the Cardiac Hypertrophic Response by Modulating Gsk3β Activity", Nature Medicine, (2007), vol. 13, No. 3, pp. 324-331.

Wilson, A-J. et al., "Histone Deacetylase 3(HDAC3) and Other Class I HDACs Regulate Colon Cell Maturation and p21 Expression and Are Deregulated in Human Colon Cancer", The Journal of Biological Chemistry, 2006, vol. 281, No. 19, pp. 13548-13558.

Sakuma, T. et al., "Aberrant Expression of Histone Deacetylase 6 in Oral Squamous Cell Carcinoma", International Journal of Oncology, 2006, vol. 29, pp. 117-124.

Glaros, S. et al., "The Reversible Epigenetic Silencing of BRM: Implications for Clinical Targeted Therapy", Oncogene, (2007), vol. 26, pp. 7058-7066.

Mai, A. et al., "Novel Pyrrole-Containing Histone Deacetylase Inhibitors Endowed with Cytodifferentiation Activity", The International Journal of Biochemistry & Cell Biology, (2007), vol. 39, pp. 1510-1522.

Vincent, A. et al., "Epigenetic Regulation(DNA Methylation, Histone Modifications) of the 11p15 Mucin Genes (MUC2, MUC5AC, MUC5AC, MUC5B, MUC6) in Epithelial Cancer Cells", Oncogene, (2007), vol. 26, pp. 6566-6576.

Herman, D. et al., "Histone Deacetylase Inhibitors Reverse Gene Silencing in Friedreich's Ataxia", Nature Chemical Biology, 2006, vol. 2, No. 10, pp. 551-559.

Avila, A. M. et al., "Trichostatin A Increases SMN Expression and Survival in a Mouse Model of Spinal Muscular Atrophy", The Journal of Clinical Investigation, 2007, vol. 117, No. 3, pp. 659-671.

De Bore, J. et al., "Inhibition of Histone Acetylation as a Tool in Bone Tissue Engineering", Tissue Engineering, (2006), vol. 12, No. 10, pp. 2927-2937.

Gialitakis, M. et al., "Coordinated Changes of Histone Modifications and HDAC Mobilization Regulate the Induction of MHC Class II Genes by Trichostatin A", Nucleic Acids Research, 2006, vol. 34, No. 3, pp. 765-772.

* cited by examiner

2-INDOLINONE DERIVATIVES AS MULTI-TARGET PROTEIN KINASE INHIBITORS AND HISTONE DEACETYLASE INHIBITORS

FIELD OF INVENTION

The present invention relates to 2-indolinone derivatives which are capable of inhibiting protein kinases and histone deacetylases. The compounds of this invention are therefore useful in treating diseases associated with abnormal protein kinase activities or abnormal histone deacetylase activities. Pharmaceutical compositions comprising these compounds, methods of treating diseases utilizing pharmaceutical compositions comprising these compounds, and methods of preparing these compounds are also disclosed.

BACKGROUND OF THE INVENTION

The favorite metaphor for cancer drug developers has long been target therapy, wherein a drug is designed to hit tumor cells at one specific target, knocking them out while leaving normal cells undamaged. Cancer cells, however, can use multiple biological triggers and pathways to grow and spread throughout the body. Hitting cancer cells at one target will allow them to regroup and redeploy along new growth paths. This realization has led to the development of combination target therapies, which are becoming the new paradigm for cancer treatment.

Several multi-target kinase inhibitors are now in development, two, (Sorafenib and Suten) are already approved in the United States. Sorafenib, developed by Bayer Pharmaceuticals, is the first drug targeting both the RAF/MEK/ERK pathway (involved in cell proliferation) and the VEGFR2/PDGFRβ signaling cascade (involved in angiogenesis). Sorafenib was first approved in December 2005 for advanced kidney cancer, a disease that is believed to be highly dependent on angiogenesis. Although some of these target therapies have been found to be effective against solid tumors, they remain far from satisfactory in terms of achieving better efficacy and minimizing treatment side-effects. Thus, the search for target therapies continues. One option is develop agents that inhibit protein kinsases as well as histone deacetylases.

Protein kinases are a family of enzymes that catalyze the phosphorylation of proteins, in particular the hydroxy group of specific tyrosine, serine and threonine residues in proteins. Protein kinases play a critical role in the regulation of a wide variety of cellular processes, including metabolism, cell proliferation, cell differentiation, cell survival, environment-host reactions, immune responses, and angiogenesis. Many diseases are associated with abnormal cellular responses triggered by protein kinase—mediated events. These diseases include inflammatory diseases, autoimmune diseases, cancer, neurological and neurodegenerative diseases, cardiovascular diseases, allergies and asthma or hormone-related disease (Tan, S-L., 2006, *J. Immunol.*, 176: 2872-2879; Healy, A. ea al., 2006, *J. Immunol.*, 177: 1886-1893; Salek-Ardakani, S. et al., 2005, *J. Immunol.*, 175: 7635-7641; Kim, J. et al., 2004, *J. Clin. Invest.*, 114: 823-827). Therefore, considerable effort has been made to identify protein kinase inhibitors that are effective as therapeutic agents against these diseases.

The protein kinases can be conventionally divided into two classes, the protein tyrosine kinases (PTKs) and the serine-threonine kinases (STKs).

The protein tyrosine kinases (PTKs) are divided into two classes: the non-transmembrane tyrosine kinases and trans-membrane growth factor receptor tyrosine kinases (RTKs).

At present, at least nineteen distinct subfamilies of RTKs have been identified, such as the epidermal growth factor receptor (EGFR), the vascular endothelial growth factor receptor (VEGFR), the platelet derived growth factor receptor growth factor receptor (PDGFR), and the fibroblast growth factor receptor (FGFR).

The epidermal growth factor receptor (EGFR) family comprises four transmembrane tyrosine kinase growth factor receptors: HER1, HER2, HER3 and HER4. Binding of a specific set of ligands to the receptor promotes EGFR dimerization and results in the receptors autophosphorylation on tyrosine residues (Arteaga, C-L., 2001, *Curr. Opin. Oncol.*, 6: 491-498). Upon autophosphorylation of the receptor several signal transduction pathways downstream of EGFR become activated. The EGFR signal transduction pathways have been implicated in the regulation of various neoplastic processes, including cell cycle progression, inhibition of apoptosis, tumor cell motility, invasion and metastasis. EGFR activation also stimulates vascular endothelial growth factor (VEGF), which is the primary inducer of angiogenesis (Petit, A-M. et al., 1997, *Am. J. Pathol.*, 151: 1523-1530). In experimental models, deregulation of the EGFR-mediated signal transduction pathways is associated with oncogenesis (Wikstrand, C-J. et al., 1998, *J Natl Cancer Inst.*, 90: 799-800). Mutations leading to continuous activation of amplification and over expression of EGFR proteins are seen in many human tumors, including tumors of breast, lung, ovaries and kidney. These mutations are a determinant of tumor aggressiveness (Wikstrand, C-J. et al., 1998, *J Natl Cancer Inst.*, 90: 799-800). EGFR over expression is frequently seen in non-small cell lung cancer (NSCLC). Activity of EGFR can be inhibited either by blocking the extracellular ligand binding domain with the use of anti-EGFR antibodies or by the use of small molecules that inhibit the EGFR tyrosine kinase, thus resulting in inhibition of downstream components of the EGFR pathway (Mendelsohn, J., 1997, *Clin. Can. Res.*, 3: 2707-2707).

The vascular endothelial growth factor (VEGF) is secreted by almost all solid tumors and tumor associated stroma in response to hypoxia. It is highly specific for vascular endothelium and regulates both vascular proliferation and permeability. Excessive expression of VEGF levels correlate with increased microvascular density, cancer recurrence and decreased survival (Parikh, A-A., 2004;, *Hematol. Oncol. Clin. N. Am.*, 18:951-971). There are 6 different ligands for the VEGF receptor, VEGF-A through -E and placenta growth factor. Ligands bind to specific receptors on endothelial cells, mostly VEGFR-2. The binding of VEGF-A to VEGFR-1 induces endothelial cell migration. Binding to VEGFR-2 induces endothelial cell proliferation, permeability and survival. VEGFR-3 is thought to mediate lymphangiogenesis. The binding of VEGF to VEGFR-2 receptors results in activation and autophosphorylation of intracellular tyrosine kinase domains which further triggers other intracellular signaling cascades (Parikh, A-A., 2004, *Hematol. Oncol. Clin. N. Am.*, 18:951-971).

The serine-threonine kinases (STKs) are predominantly intracellular although there are a few receptor kinases of the STK type. STKs are the most common forms of the cytosolic kinases that perform their function in the part of the cytoplasm other than the cytoplasmic organelles and cytoskelton.

Glycogen synthase kinase-3 (GSK-3) is a serine-threonine protein kinase comprised of α and β isoforms that are each encoded by distinct genes. GSK-3 has been found to phosphorylate and modulate the activity of a number of regulatory proteins. GSK-3 has been implicated in various diseases including diabetes, Alzheimer's disease, CNS disorders such as manic depressive disorder and neurodegenerative diseases, and cardiomyocyte hypertrophy (Haq, et al., 2000, *J. Cell Biol.*, 151: 117).

Aurora-2 is a serine-threonine protein kinase that has been implicated in human cancer, such as colon, breast, and other solid tumors. This kinase is believed to be involved in protein phosphorylation events that regulate cell cycle. Specifically, Aurora-2 may play a role in controlling the accurate segregation of chromosomes during mitosis. Misregulation of the cell cycle can lead to cellular proliferation and other abnormalities. In human colon cancer tissue, the Aurora-2 protein has been found to be over expressed (Schumacher, et al., 1998, *J. Cell Biol.*, 143: 1635-1646; Kimura et al., 1997, *J. Biol. Chem.*, 272: 13766-13771).

The cyclin-dependent kinases (CDKs) are serine-threonine protein kinase that regulate mammalian cell division. CDKs play a key role in regulating cell machinery. To date, nine kinase subunits (CDK 1-9) have been identified. Each kinase associates with a specific regulatory partner which together make up the active catalytic moiety. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers.

Raf kinase, a downstream effector of ras oncoprotein, is a key mediator of signal-transduction pathways from cell surface to the cell nucleus. Inhibition of raf kinase has been correlated in vitro and in vivo with inhibition of the growth of variety of human tumor types (Monia et al., 1996, *Nat. Med.*, 2: 668-675).

Other serine-threonine protein kinases include the protein kinase A, B and C. These kinases, known as PKA, PKB and PKC, play key roles in signal transduction pathways.

Many attempts have been made to identify small molecules which act as protein kinase inhibitors useful in the treatment of diseases associated with abnormal protein kinase activities. For example, cyclic compounds (U.S. Pat. No. 7,151,096), bicyclic compounds (U.S. Pat. No. 7,189,721), tricyclic compounds (U.S. Pat. No. 7,132,533), (2-oxindol-3-ylidenyl) acetic acid derivatives (U.S. Pat. No. 7,214,700), 3-(4-amidopyrrol-2-ylmethlidene)-2-indolinone derivatives (U.S. Pat. No. 7,179,910), fused pyrazole derivatives (U.S. Pat. No. 7,166,597), aminofurazan compounds (U.S. Pat. No. 7,157,476), pyrrole substituted 2-indolinone compounds (U.S. Pat. No. 7,125,905), triazole compounds (U.S. Pat. No. 7,115,739), pyrazolylamine substituted quinazoline compounds (U.S. Pat. No. 7,098,330) and indazole compounds (U.S. Pat. No. 7,041,687) have all been described as protein kinase inhibitors. Several protein kinase inhibitors such as Glivec, Suten, and Sorafenib have been successfully approved by the FDA as anti-cancer therapies. Their clinical use demonstrated clear advantages over existing chemotherapeutical treatments, fueling continuing interest in the innovation of mechanism-based treatments using new compounds with chemical scaffold improvements with excellent oral bioavailability, significant anti-tumor activity, and lower toxicity at well-tolerated dose.

Histone deacetylase (HDAC) proteins play a critical role in regulating gene expression in vivo by altering the accessibility of genomic DNA to transcription factors. Specifically, HDAC proteins remove the acetyl group of acetyl-lysine residues on histones, which can result in nucleosomal remodelling (Grunstein, M., 1997, *Nature*, 389: 349-352). Due to their governing role in gene expression, HDAC proteins are associated with a variety of cellular events, including cell cycle regulation, cell proliferation, differentiation, reprogramming of gene expression, and cancer development (Ruijter, A-J·M., 2003, Biochem. J., 370: 737-749; Grignani, F., 1998, Nature, 391: 815-818; Lin, R-J., 1998, 391: 811-814; Marks, P-A., 2001, Nature Reviews Cancer, 1: 194). In fact, HDAC inhibitors have been demonstrated to reduce tumor growth in various human tissues and in animal studies, including lung, stomach, breast, and prostrate (Dokmanovic, M., 2005, J. Cell Biochenm., 96: 293-304).

Mammalian HDACs can be divided into three classes according to sequence homology. Class I consists of the yeast Rpd3-like proteins (HDAC 1, 2, 3, 8 and 11). Class II consists of the yeast HDA1-like proteins (HDAC 4, 5, 6, 7, 9 and 10). Class III consists of the yeast SIR2-like proteins (SIRT 1, 2, 3, 4, 5, 6 and 7).

The activity of HDAC1 has been linked to cell proliferation, a hallmark of cancer. Particularly, mammalian cells with knock down of HDAC1 expression using siRNA were anti-proliferative (Glaser, K-B., 2003, *Biochem. Biophys. Res. Comm.*, 310: 529-536). While the knock out mouse of HDAC1 was embryonic lethal, the resulting stem cells displayed altered cell growth (Lagger, G., 2002, *EMBO J.*, 21: 2672-2681). Mouse cells overexpressing HDAC1 demonstrated a lengthening of $G_2$ and M phases and reduced growth rate (Bartl. S., 1997, Mol. Cell Biol., 17: 5033-5043). Therefore, the reported data implicate HDAC1 in cell cycle regulation and cell proliferation.

HDAC2 regulates expression of many fetal cardiac isoforms. HDAC2 deficiency or chemical inhibition of histone deacetylase prevented the re-expression of fetal genes and attenuated cardiac hypertrophy in hearts exposed to hypertrophic stimuli. Resistance to hypertrophy was associated with increased expression of the gene encoding inositol polyphosphate-5-phosphatase f (Inpp5f) resulting in constitutive activation of glycogen synthase kinase 3β (Gsk3β) via inactivation of thymoma viral proto-oncogene (Akt) and 3-phosphoinositide-dependent protein kinase-1 (Pdk1). In contrast, HDAC2 transgenic mice had augmented hypertrophy associated with inactivated Gsk3β. Chemical inhibition of activated Gsk3β allowed HDAC2-deficient adults to become sensitive to hypertrophic stimulation. These results suggest that HDAC2 is an important molecular target of HDAC inhibitors in the heart and that HDAC2 and Gsk3β are components of a regulatory pathway providing an attractive therapeutic target for the treatment of cardiac hypertrophy and heart failure (Trivedi, C-M., 2007, *Nat. Med.* 13: 324-331).

HDAC3 are maximally expressed in proliferating crypt cells in normal intestine. Silencing of HDAC3 expression in colon cancer cell lines resulted in growth inhibition, a decrease in cell survival, and increased apoptosis. Similar effects were observed for HDAC2 and, to a lesser extent, for HDAC1. HDAC3 gene silencing also selectively induced expression of alkaline phosphatase, a marker of colon cell maturation. Concurrent with its effect on cell growth, overexpression of HDAC3 inhibited basal and butyrate-induced p21 transcription in a Sp1/Sp3-dependent manner, whereas silencing of HDAC3 stimulated p21 promoter activity and expression. These findings identify HDAC3 as a gene deregulated in human colon cancer and as a novel regulator of colon cell maturation and p21 expression (Wilson, A-J., 2006, *J. Biol. Chem.*, 281: 13548-13558).

HDAC6 is a subtype of the HDAC family that deacetylates alpha-tubulin and increases cell motility. Using quantitative real-time reverse transcription polymerase chain reaction and Western blots on nine oral squamous cell carcinoma (OSCC)-derived cell lines and normal oral keratinocytes (NOKs), HDAC6 mRNA and protein expression were commonly up-regulated in all cell lines compared with the NOKs. Immunofluorescence analysis detected HDAC6 protein in the cytoplasm of OSCC cell lines. Similar to OSCC cell lines, high frequencies of HDAC6 up-regulation were evident in both mRNA (74%) and protein (51%) levels of primary human OSCC tumors. Among the clinical variables analyzed, the clinical tumor stage was found to be associated with the HDAC6 expression states. The analysis indicated a significant difference in the HDAC6 expression level between the early stage (stage I and II) and advanced-stage (stage III and IV) tumors (P=0.014). These results suggest that HDAC6 expression may be correlated with tumor aggressiveness and offer clues to the planning of new treatments (Sakuma, T., 2006, *Int. J. Oncol.*, 29: 117-124).

Epigenetic silencing of functional chromosomes by HDAC is one of the major mechanisms that occurrs in pathological processes in which functionally critical genes are repressed or reprogrammed by HDAC activities leading to the loss of phenotypes in terminal differentiation, maturation and growth control, and the loss of functionality of tissues. For example, tumor suppressor genes are often silenced during development of cancer and chemical inhibitors of HDAC can derepress the expression of these tumor suppressor genes, leading to growth arrest and differentiation (Glaros S et al., 2007, Oncogene June 4 Epub ahead of print; Mai, A, et al., 2007, Int J. Biochem Cell Bio., April 4, Epub ahead of print; Vincent A. et al., 2007, Oncogene, April 30, Epub ahead of print; our unpublished results). Repression of structural genes such as FXN in Friedreich's ataxia and SMN in spinal muscular atrophy can be reversed by HDAC inhibitors, leading to re-expression and resumption of FXN and SMN gene function in tissues (Herman D et al., 2006, Nature Chemical Biology, 2(10):551-8; Avila AM et al., 2007, J Clinic Investigation, 117(3)659-71; de Bore J, 2006, Tissue Eng. 12(10): 2927-37); Induction of the entire MHC II family gene expression through reprogramming of HDAC "hot spot" in chromosome 6p21-22 by HDAC inhibitors further extends epigenetic modulation of immune recognition and immune response (Gialitakis M et al., 2007, Nucleic Acids Res., 34(1); 765-72).

Several classes of HDAC inhibitors have been identified, including (1) short-chain fatty acids, e.g. butyrate and phenylbutyrate; (2) organic hydroxamic acids, e.g. suberoylanilide hydroxamic acid (SAHA) and trichostatin A (TSA); (3) cyclic tetrapeptides containing a 2-amino-8-oxo 9,10-expoxydecanoyl (AOE) moiety, e.g. trapoxin and HC-toxin; (4) cyclic peptides without the AOE moiety, e.g. apicidin and FK228; and (5) benzamides, e.g. MS-275 (EP0847992A1, US2002/0103192A1, WO02/26696A1, WO01/70675A2, WO01/18171A2). HDAC represents a very promising drug target especially in the context of epigenic biology; for example, in terms of preferential apoptosis-induction in malignant cells but not normal cells, differentiation of epithelia in cancer cells, anti-inflammatory and immunomodulation, and cell cycle arrest.

The use of HDAC inhibitors can be considered as "neo-chemotherapy" having a much improved toxicity profile over existing chemotherapy options. The success of SAHA from Merck is currently only limited to the treatment of cutaneous T cell lymphoma. No reports exist indicating that SAHA treatment is effective against major solid tumors or for any other indications. Therefore, there is still a need to discover new compounds with improved profiles, such as stronger HDAC inhibitory activity and anti-cancer activity, more selective inhibition on different HDAC subtypes, and lower toxicity; There is a continuing need to identify novel HDAC inhibitors that can be used to treat potential new indications such as neurological and neurodegenerative disorders, cardiovascular disease, metabolic disease, and inflammatory and immunological diseases.

SUMMARY OF THE INVENTION

The present invention is directed to certain 2-indolinone derivatives which are capable of selectively inhibiting protein kinases and histone deacetylases and are therefore useful in treating diseases associated with abnormal protein kinase activities and abnormal histone deacetylase activities. In particular, the compounds are highly effective against hematological malignancy and solid carcinomas.

DETAILED DESCRIPTION OF THE INVENTION

Various publications are cited throughout the present application. The contents of these publications and contents of documents cited in these publications are incorporated herein by reference.

Provided herein are new chemical compounds that combine anti-angiogenesis and anti-proliferation activities of RTK's together with differentiation-inducing, immune modulation, cell cycle arrest and apoptosis-induction activities of more selective HDACi, to reach a better efficacy against solid tumors while overcoming side effects such as hypertension, QT prolongation, thyroid gland regression, skin rash and discoloration, and pains associated with currently marketed RTK inhibitors.

Particularly, the present invention provides a compound having the structure represented by formula (I), or its stereoisomer, enantiomer, diastereomer, hydrate, or pharmaceutically acceptable salts thereof:

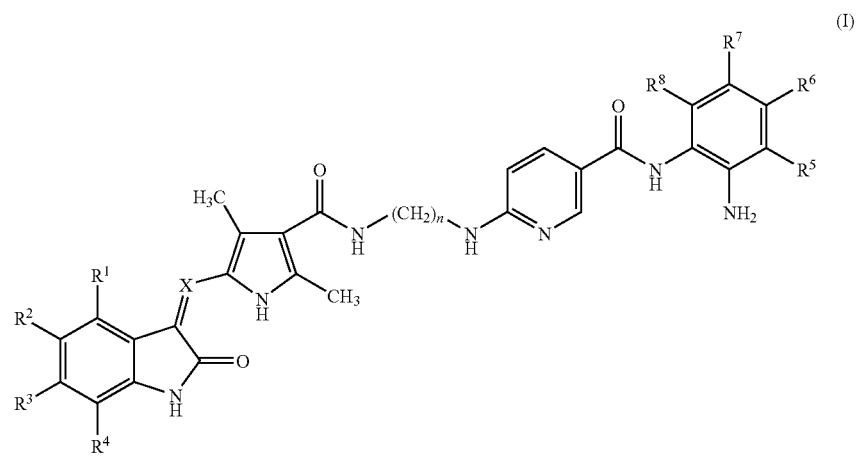

wherein
X is =CH— or =N—N=CH—;
$R^1$, $R^2$, $R^3$ and $R^4$ are independently hydrogen, halo, alkyl alkoxy, nitro or trifluoromethyl;
$R^5$, $R^6$, $R^7$ and $R^8$ are independently hydrogen, halo, alkyl alkoxy or trifluoromethyl; n is an integer ranging from 2 to 6.

In the above structural formula (I) and throughout the present specification, the following terms have the indicated meaning:

The term "halo" as used herein means fluorine, chlorine, bromine or iodine.

The term "alkyl" as used herein includes methyl, ethyl, n-propyl, iso-propyl, butyl, iso-butyl, sec-butyl, tert-butyl and the like.

The term "alkoxy" as used herein includes methoxy, ethoxy, n-propoxy, isopropoxy, n-butoxy, isobutoxy and the like.

In one embodiment of a compound of formula (I), X is =CH—; $R^1$, $R^2$, $R^3$ and $R^4$ are independently hydrogen, halo, alkyl alkoxy, nitro or trifluoromethyl; $R^5$, $R^6$, $R^7$ and $R^8$ are independently hydrogen, halo, alkyl alkoxy or trifluoromethyl; and n is an integer ranging from 2 to 4.

In another embodiment, X is =CH—; $R^1$, $R^2$, $R^3$ and $R^4$ are independently hydrogen, halo, alkyl alkoxy, nitro or trifluoromethyl; $R^5$, $R^6$, $R^7$ and $R^8$ are independently H or F; and n is an integer ranging from 2 to 4.

In another embodiment, X is =N—N=CH—; $R^1$, $R^2$, $R^3$ and $R^4$ are independently hydrogen, halo, alkyl alkoxy, nitro or trifluoromethyl; $R^5$, $R^6$, $R^7$ and $R^8$ are independently hydrogen, halo, alkyl alkoxy or trifluoromethyl; and n is an integer ranging from 2 to 4.

In another embodiment, X is =N—N=CH—; $R^1$, $R^2$ $R^3$ and $R^4$ are independently hydrogen, halo, alkyl alkoxy, nitro or trifluoromethyl; $R^5$, $R^6$, $R^7$ and $R^8$ are independently H or F; and n is an integer ranging from 2 to 4.

The compounds of this invention are prepared as described below:

(a) 6-Chloronicotinic acid is condensed with compound 1 to give compound 2;

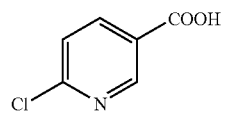

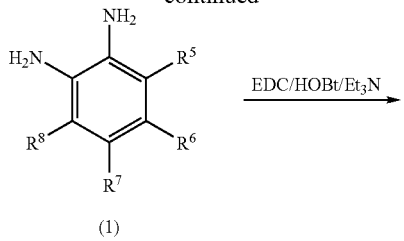

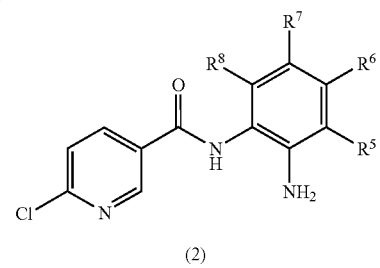

(b) Compound 2 is condensed with compound 3 to give compound 4;

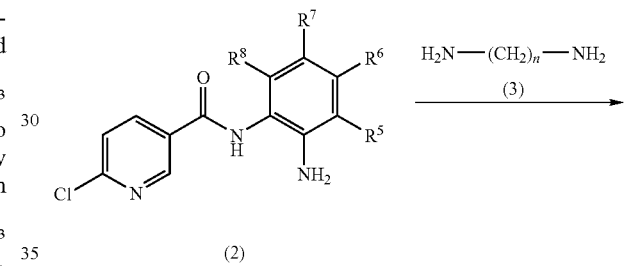

(c) Compound 4 is condensed with compound 5 to give compound 6.

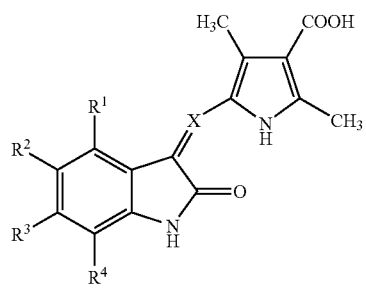

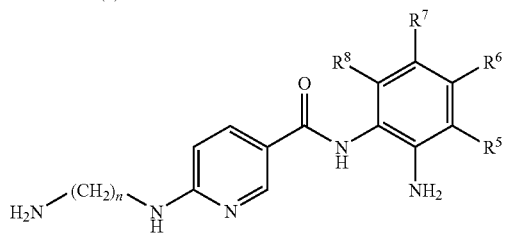

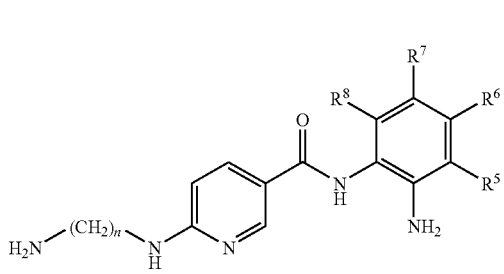

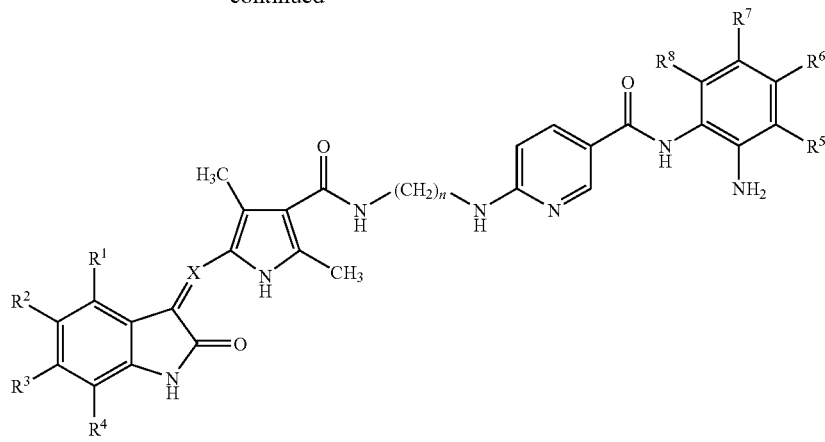

(6)

Condensation reactions (a) and (c) are conducted by using a peptide condensing agent such as 1-ethyl-3-(3-dimethylaminopropyl)carbodiimide (EDC), dicyclohexylcarbodiimide (DCC), N,N'-carbonyldiimidazole (CDI), etc. The reaction may be conducted at 0 to 80° C. for 4 to 72 hours. Solvents which may be used are normal solvents such as benzene, toluene, tetrahydrofuran, dioxane, dichloromethane, chloroform, N,N-dimethylformamide, etc. If necessary, a base such as sodium hydroxide, triethylamine and pyridine may be added to the reaction system.

Condensation reaction (b) is conducted at 40 to 120° C. for 1 to 24 hours. Solvents which may be used are normal solvents such as benzene, toluene, tetrahydrofuran, dioxane, dichloromethane, chloroform, N,N-dimethylformamide, etc. If necessary, a base such as sodium hydroxide, triethylamine and pyridine may be added to the reaction system.

The compounds represented by formula (I) and the intermediate (2) and (4) may be purified or isolated by the conventional separation methods such as extraction, recrystallization, column chromatography and the like.

The compounds represented by formula (I) are capable of inhibiting protein kinases and histone deacetylases and are therefore useful in treating diseases associated with abnormal protein kinase activities and abnormal histone deacetylase activities. In particular, they are highly effective against hematological malignancy and solid carcinomas.

The compounds represented by formula (I) useful as a drug may be used in the form of a general pharmaceutical composition. The pharmaceutical composition may be in the forms normally employed, such as tablets, capsules, powders, syrups, solutions, suspensions, aerosols, and the like, may contain flavorants, sweeteners etc. in suitable solids or liquid carriers or diluents, or in suitable sterile media to form injectable solutions or suspensions. Such composition typically contains from 0.5 to 70%, preferably 1 to 20% by weight of active compound, the remainder of the composition being pharmaceutically acceptable carriers, diluents or solvents or salt solutions.

The compounds represented by formula (I) are clinically administered to mammals, including man and animals, via oral, nasal, transdermal, pulmonary, or parenteral routes. Administration by the oral route is preferred, being more convenient and avoiding the possible pain and irritation of injection. By either route, the dosage is in the range of about 0.0001 to 200 mg/kg body weight per day administered singly or as a divided dose. However, the optimal dosage for the individual subject being treated will be determined by the person responsible for treatment, generally smaller dose being administered initially and thereafter increments made to determine the most suitable dosage.

Representative compounds of the present invention are shown in Table 1 below. The compound numbers correspond to the "Example numbers" in the Examples section. That is, the synthesis of compound 3 as shown in the Table 1 is described in "Example 3" and the synthesis of compound 51 as shown in the Table 1 is described in "Example 51". The compounds presented in the Table 1 are exemplary only and are not to be construed as limiting the scope of this invention in any manner.

TABLE 1

| Example | Structure | Name |
|---|---|---|
| 3 | 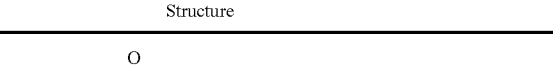 | (Z)-N-(2-Aminophenyl)-6-(2-(2-((5-fluoro-2-oxoindolin-3-ylidene)-methyl)-3,5-dimethyl-1H-pyrrole-4-carboxamido)-ethylamino)-nicotinamide |

TABLE 1-continued

| Example | Structure | Name |
|---|---|---|
| 4 | 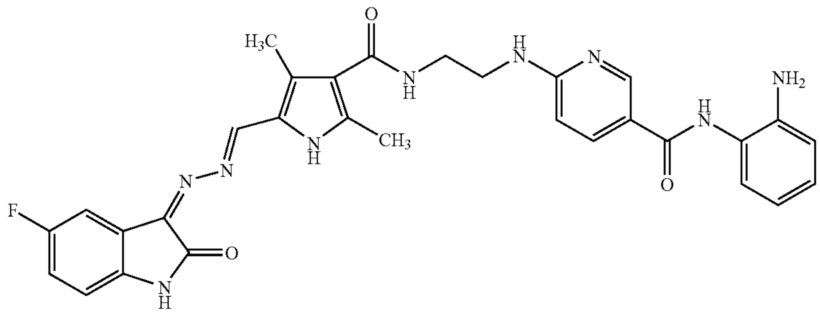 | N-(2-Aminophenyl)-6-(2-(2-(((5-fluoro-2-oxoindolin-3-ylidene)-hydrazono)methyl)-3,5-dimethyl-1H-pyrrole-4-carboxamido)-ethylamino)nicotinamide |
| 6 | 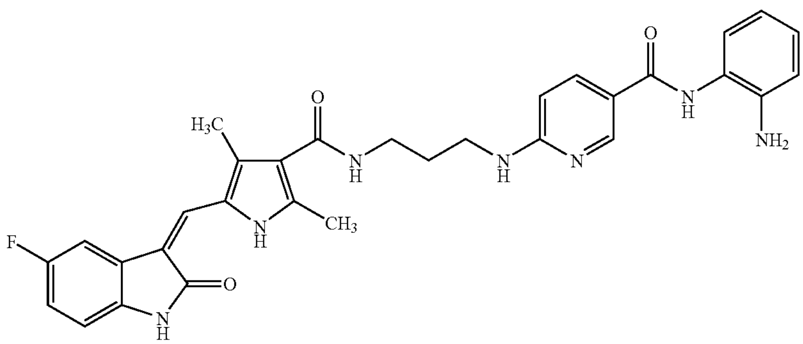 | (Z)-N-(2-Aminophenyl)-6-(3-(2-((5-fluoro-2-oxoindolin-3-ylidene)-methyl)-3,5-dimethyl-1H-pyrrole-4-carboxamido)-propylamino)-nicotinamide |
| 7 | 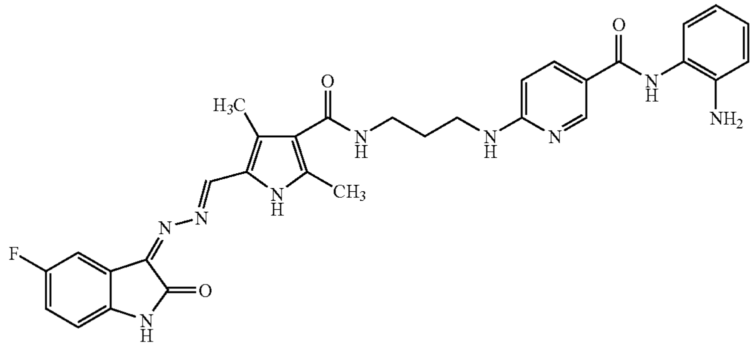 | N-(2-Aminophenyl)-6-(3-(2-(((5-fluoro-2-oxoindolin-3-ylidene)-hydrazono)methyl)-3,5-dimethyl-1H-pyrrole-4-carboxamido)-propylamino)nicotinamide |
| 9 | 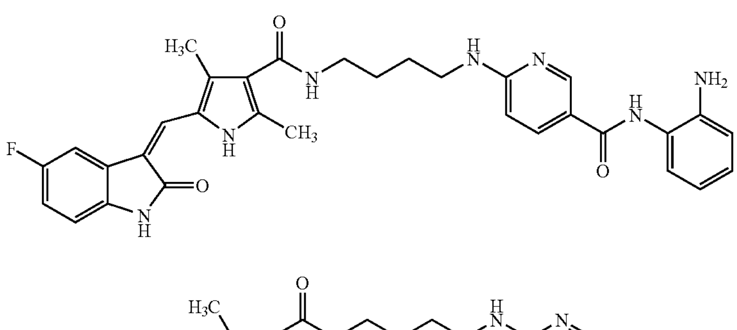 | (Z)-N-(2-Aminophenyl)-6-(4-(2-((5-fluoro-2-oxoindolin-3-ylidene)-methyl)-3,5-dimethyl-1H-pyrrole-4-carboxamido)-butylamino)-nicotinamide |
| 10 | 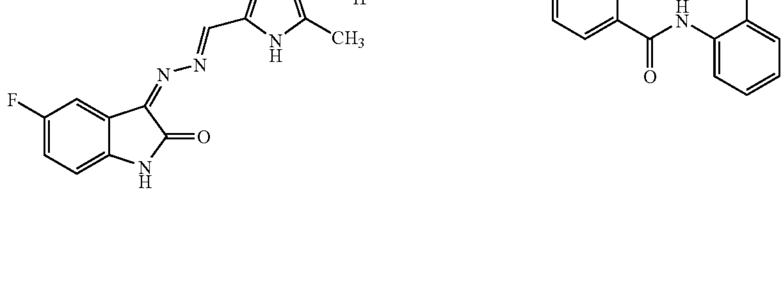 | N-(2-Aminophenyl)-6-(4-(2-(((5-fluoro-2-oxoindolin-3-ylidene)-hydrazono)methyl)-3,5-dimethyl-1H-pyrrole-4-carboxamido)-butylamino)nicotinamide |

TABLE 1-continued

| Example | Structure | Name |
|---------|-----------|------|
| 13 | 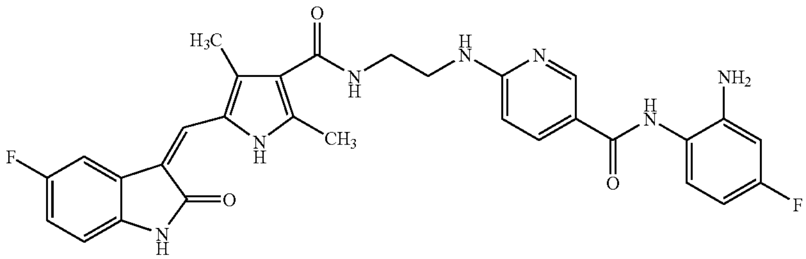 | (Z)-N-(2-Amino-4-fluorophenyl)-6-(2-(2-((5-fluoro-2-oxoindolin-3-ylidene)-methyl)-3,5-dimethyl-1H-pyrrole-4-carboxamido)-ethylamino)nicotinamide |
| 14 | 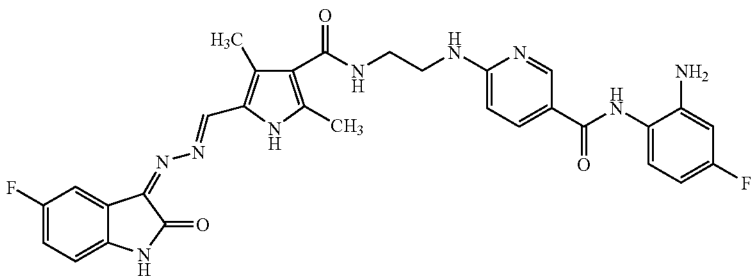 | N-(2-Amino-4-fluorophenyl)-6-(2-(2-(((5-fluoro-2-oxoindolin-3-ylidene)hydrazono)methyl)-3,5-dimethyl-1H-pyrrole-4-carboxamido)ethylamino)-nicotinamide |
| 16 | 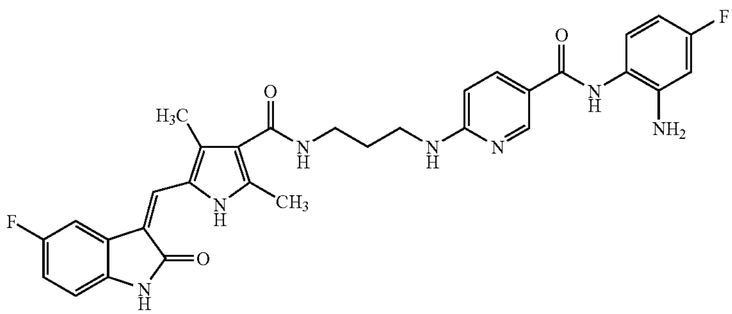 | (Z)-N-(2-Amino-4-fluorophenyl)-6-(3-(2-((5-fluoro-2-oxoindolin-3-ylidene)methyl)-3,5-dimethyl-1H-pyrrole-4-carboxamido)-propyl-amino)nicotinamide |
| 17 | 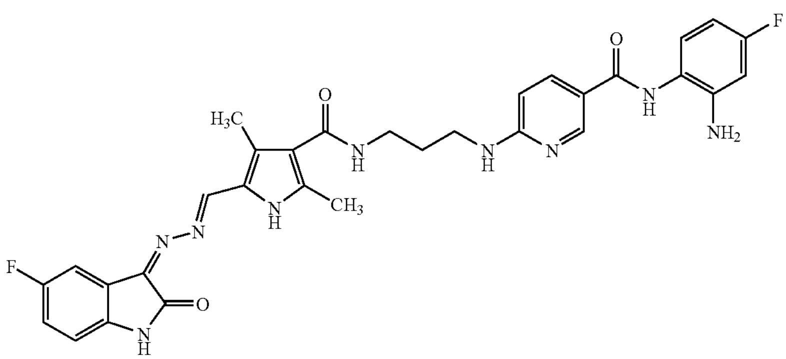 | N-(2-Amino-4-fluorophenyl)-6-(3-(2-(((5-fluoro-2-oxoindolin-3-ylidene)hydrazono)methyl)-3,5-dimethyl-1H-pyrrole-4-carboxamido)propylamino)-nicotinamide |
| 19 | 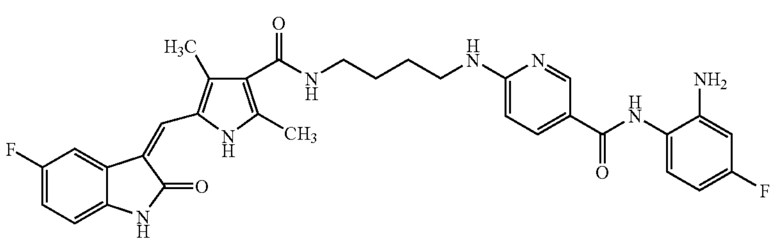 | (Z)-N-(2-Amino-4-fluorophenyl)-6-(4-(2-((5-fluoro-2-oxoindolin-3-ylidene)methyl)-3,5-dimethyl-1H-pyrrole-4-carboxamido)butyl-amino)nicotinamide |

TABLE 1-continued

| Example | Structure | Name |
|---|---|---|
| 20 | 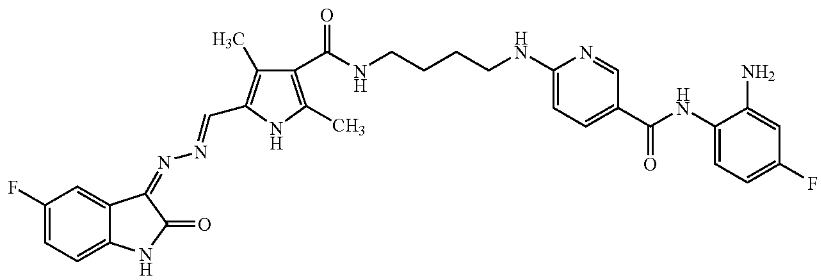 | N-(2-Amino-4-fluorophenyl)-6-(4-(2-(((5-fluoro-2-oxoindolin-3-ylidene)hydrazono)methyl)-3,5-dimethyl-1H-pyrrole-4-carboxamido)butylamino)-nicotinamide |
| 23 | 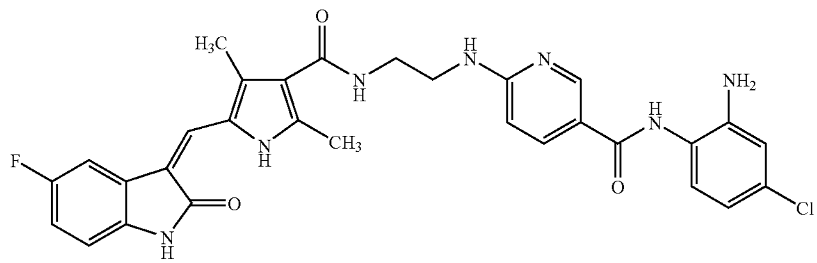 | (Z)-N-(2-Amino-4-chlorophenyl)-6-(2-(2-((5-fluoro-2-oxoindolin-3-ylidene)methyl)-3,5-dimethyl-1H-pyrrole-4-carboxamido)ethyl-amino)nicotinamide |
| 24 | 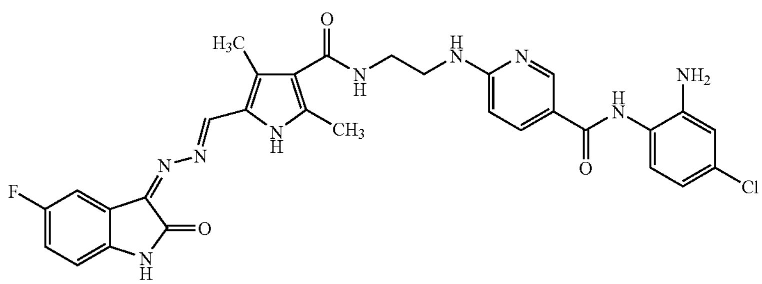 | N-(2-Amino-4-chlorophenyl)-6-(2-(2-(((5-fluoro-2-oxoindolin-3-ylidene)hydrazono)methyl)-3,5-dimethyl-1H-pyrrole-4-carboxamido)ethylamino)-nicotinamide |
| 27 | 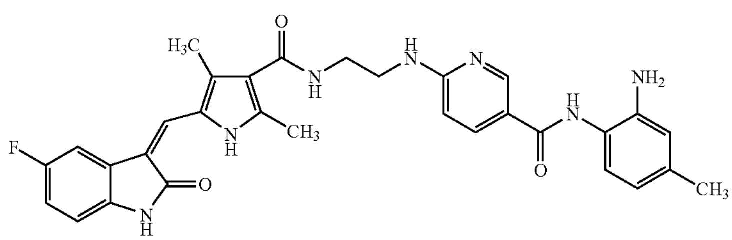 | (Z)-N-(2-Amino-4-methylphenyl)-6-(2-(2-((5-fluoro-2-oxoindolin-3-ylidene)methyl)-3,5-dimethyl-1H-pyrrole-4-carboxamido)ethyl-amino)nicotinamide |
| 28 | 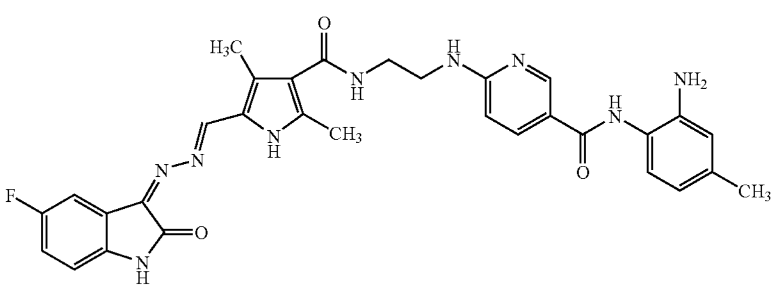 | N-(2-Amino-4-methylphenyl)-6-(2-(2-(((5-fluoro-2-oxoindolin-3-ylidene)hydrazono)methyl)-3,5-dimethyl-1H-pyrrole-4-carboxamido)ethylamino)-nicotinamide |
| 31 | 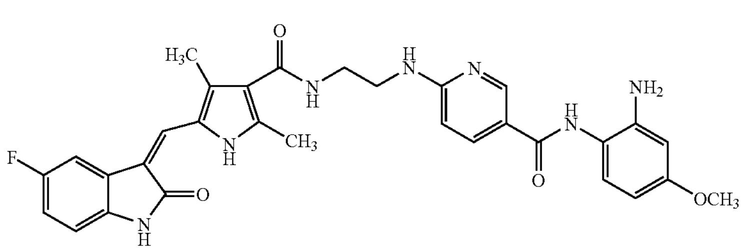 | (Z)-N-(2-Amino-4-methoxyphenyl)-6-(2-(2-((5-fluoro-2-oxoindolin-3-ylidene)methyl)-3,5-dimethyl-1H-pyrrole-4-carboxamido)ethyl-amino)nicotinamide |

TABLE 1-continued

| Example | Structure | Name |
|---|---|---|
| 32 | 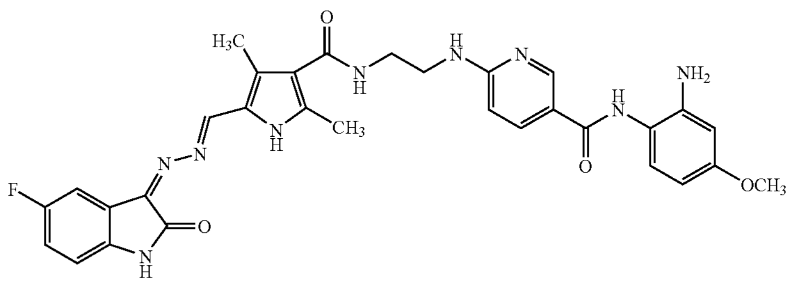 | N-(2-Amino-4-methylphenyl)-6-(2-(2-(((5-fluoro-2-oxoindolin-3-ylidene)hydrazono)methyl)-3,5-dimethyl-1H-pyrrole-4-carboxamido)ethylamino)-nicotinamide |
| 35 | 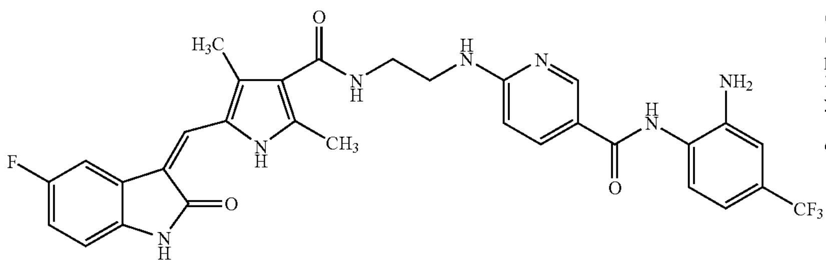 | (Z)-N-(2-Amino-4-trifluoromethyl-phenyl)-6-(2-(2-((5-fluoro-2-oxoindolin-3-ylidene)methyl)-3,5-dimethyl-1H-pyrrole-4-carboxamido)-ethylamino)-nicotinamide |
| 36 | 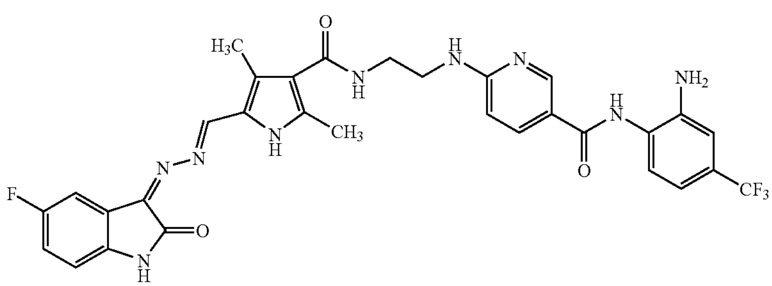 | N-(2-Amino-4-trifluoromethyl-phenyl)-6-(2-(2-(((5-fluoro-2-oxoindolin-3-ylidene)hydrazono)-methyl)-3,5-dimethyl-1H-pyrrole-4-carboxamido)ethylamino)-nicotinamide |
| 37 | 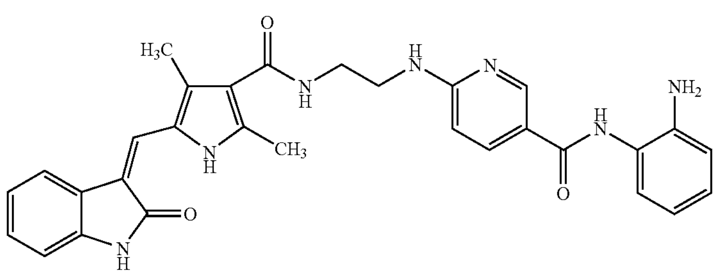 | (Z)-N-(2-Aminophenyl)-6-(2-(2-((2-oxoindolin-3-ylidene)methyl)-3,5-dimethyl-1H-pyrrole-4-carboxamido)ethylamino)-nicotinamide |
| 38 | 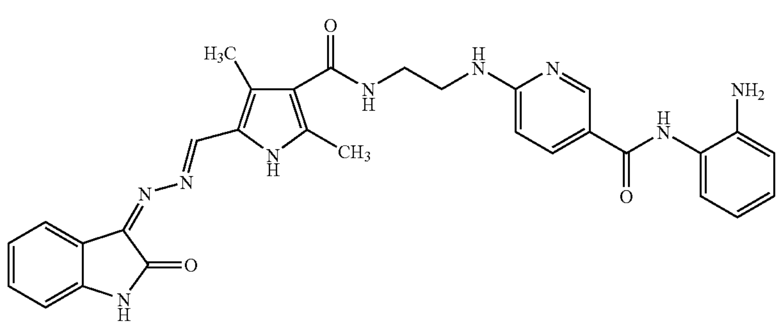 | N-(2-Aminophenyl)-6-(2-(2-(((2-oxoindolin-3-ylidene)hydrazono)-methyl)-3,5-dimethyl-1H-pyrrole-4-carboxamido)ethylamino)-nicotinamide |

TABLE 1-continued

| Example | Structure | Name |
|---|---|---|
| 39 | 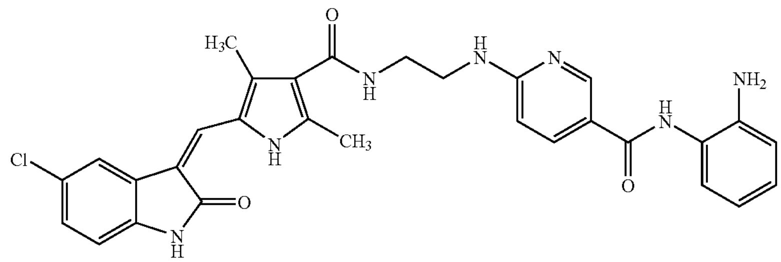 | (Z)-N-(2-Aminophenyl)-6-(2-(2-((5-chloro-2-oxoindolin-3-ylidene)-methyl)-3,5-dimethyl-1H-pyrrole-4-carboxamido)-ethylamino)-nicotinamide |
| 40 | 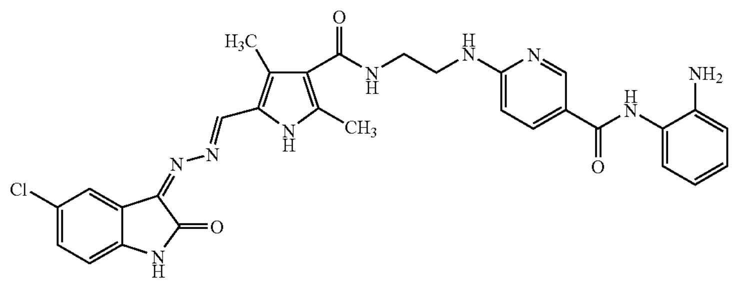 | N-(2-Aminophenyl)-6-(2-(2-(((5-chloro-2-oxoindolin-3-ylidene)-hydrazono)methyl)-3,5-dimethyl-1H-pyrrole-4-carboxamido)ethyl-amino)nicotinamide |
| 41 | 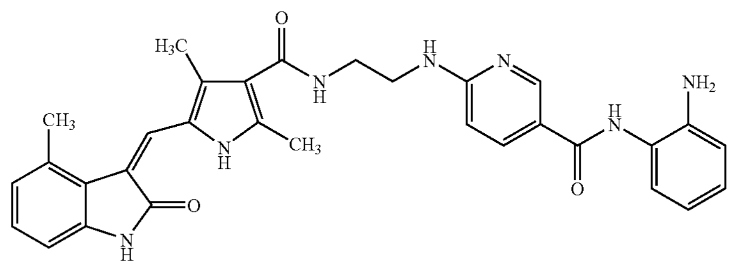 | (Z)-N-(2-Aminophenyl)-6-(2-(2-(((4-methyl-2-oxoindolin-3-ylidene)-methyl)-3,5-dimethyl-1H-pyrrole-4-carboxamido)-ethylamino)-nicotinamide |
| 42 | 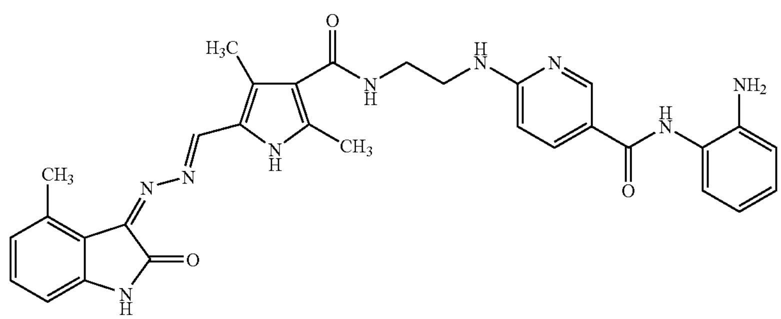 | N-(2-Aminophenyl)-6-(2-(2-(((4-methyl-2-oxoindolin-3-ylidene)-hydrazono)methyl)-3,5-dimethyl-1H-pyrrole-4-carboxamido)ethyl-amino)nicotinamide |
| 43 | 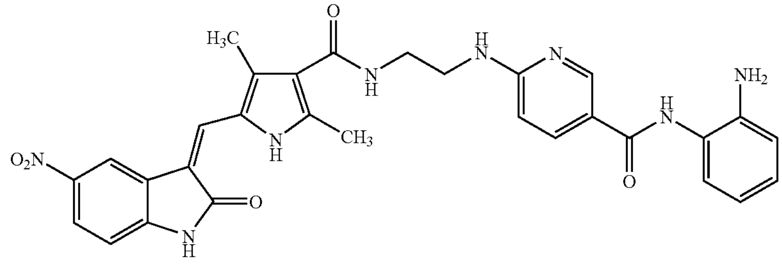 | (Z)-N-(2-Aminophenyl)-6-(2-(2-((5-nitro-2-oxoindolin-3-ylidene)-methyl)-3,5-dimethyl-1H-pyrrole-4-carboxamido)ethylamino)-nicotinamide |

TABLE 1-continued

| Example | Structure | Name |
|---|---|---|
| 44 | 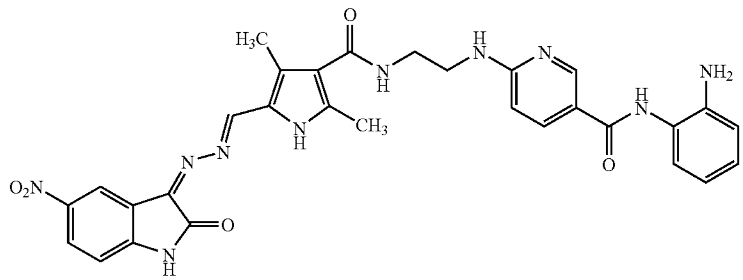 | N-(2-Aminophenyl)-6-(2-(2-(((5-nitro-2-oxoindolin-3-ylidene)-hydrazono)methyl)-3,5-dimethyl-1H-pyrrole-4-carboxamido)ethyl-amino)nicotinamide |
| 45 | 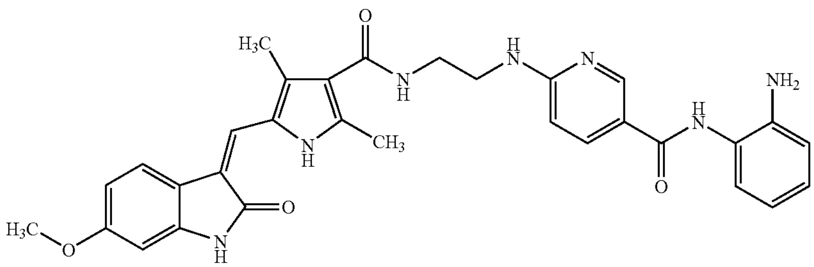 | (Z)-N-(2-Aminophenyl)-6-(2-(2-((6-methoxy-2-oxoindolin-3-ylidene)methyl)-3,5-dimethyl-1H-pyrrole-4-carboxamido)ethyl-amino)nicotinamide |
| 46 | 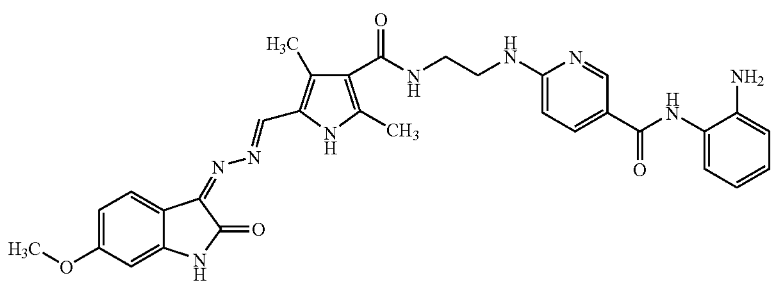 | N-(2-Aminophenyl)-6-(2-(2-(((6-methoxy-2-oxoindolin-3-ylidene)-hydrazono)methyl)-3,5-dimethyl-1H-pyrrole-4-carboxamido)ethyl-amino)nicotinamide |
| 47 | 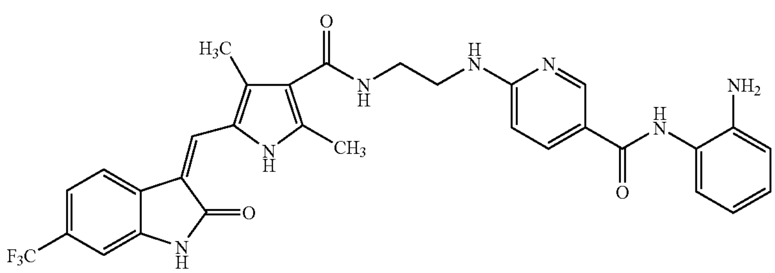 | (Z)-N-(2-Aminophenyl)-6-(2-(2-((6-trifluoromethyl-2-oxoindolin-3-ylidene)methyl)-3,5-dimethyl-1H-pyrrole-4-carboxamido)-ethyl-amino)nicotinamide |
| 48 | 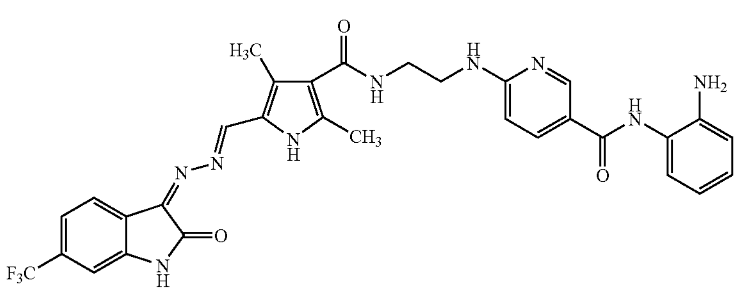 | N-(2-Aminophenyl)-6-(2-(2-(((6-trifluoromethyl-2-oxoindolin-3-ylidene)hydrazono)methyl)-3,5-dimethyl-1H-pyrrole-4-carboxamido)ethylamino)-nicotinamide |

TABLE 1-continued

| Example | Structure | Name |
|---|---|---|
| 50 | 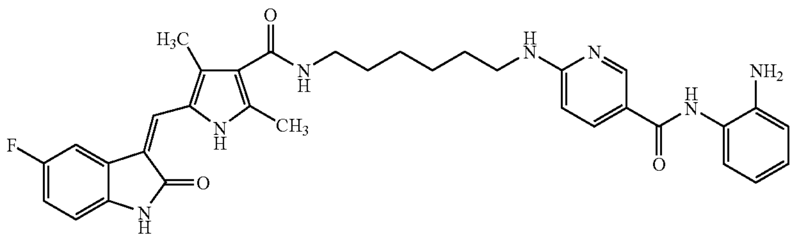 | (Z)-N-(2-Aminophenyl)-6-(6-(2-((5-fluoro-2-oxoindolin-3-ylidene)-methyl)-3,5-dimethyl-1H-pyrrole-4-carboxamido)-hexylamino)-nicotinamide |
| 51 | 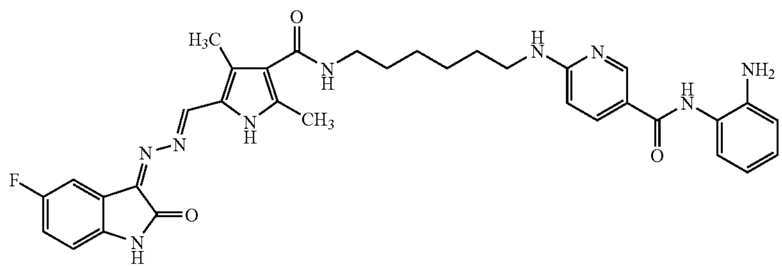 | N-(2-Aminophenyl)-6-(6-(2-(((5-fluoro-2-oxoindolin-3-ylidene)-hydrazono)methyl)-3,5-dimethyl-1H-pyrrole-4-carboxamido)hexyl-amino)nicotinamid |

Further, all parts and percentages in the examples, as well as in the remainder of the specification, are by weight unless otherwise specified. Any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result.

EXAMPLE 1

Preparation of N-(2-aminophenyl)-6-chloronicotinamide

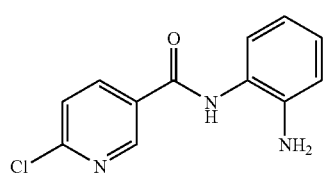

6-Chloronicotinic acid (157.5 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and o-phenylenediamine (216 mg, 2 mmol) were added. The mixture was stirred for 20 hours at room temperature. The mixture was diluted with 400 mL of brine and extracted with 200 ml of ethyl acetate. The ethyl acetate was removed under vacuum. To the residue was added 5 ml of absolute ethanol. The solids were collected by vacuum filtration, washed with absolute ethanol and dried under vacuum to give the title compound (138 mg, 56% yield) as a brown solid. LC-MS (m/z) 248 (M+1).

EXAMPLE 2

Preparation of N-(2-aminophenyl)-6-(2-aminoethylamino)nicotinamide

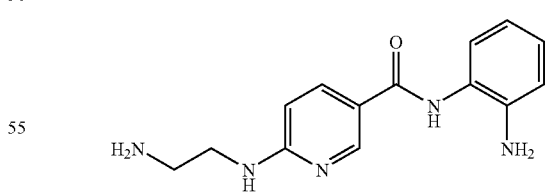

N-(2-Aminophenyl)-6-chloronicotinamide (248 mg, 1 mmol) and 5 ml of ethylenediamine were heated to 80° C. for 3 hours. The excess ethylenediamine was removed under vacuum. To the residue was added 5 ml of 0.20 M NaOH. The mixture was extracted with 100 ml of ethyl acetate. The ethyl acetate was removed under vacuum to give the title compound (150 mg, 55% yield) as a brown solid. LC-MS (m/z) 272 (M+1).

EXAMPLE 3

Preparation of (Z)-N-(2-aminophenyl)-6-(2-(2-((5-fluoro-2-oxoindolin-3-ylidene)methyl)-3,5-dimethyl-1H-pyrrole-4-carboxamido)ethylamino)nicotinamide

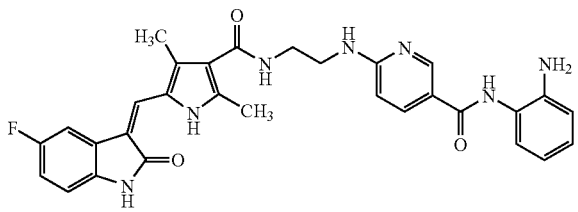

5-(5-Fluoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (493 mg, 89%) as a yellow solid. $^1$H NMR (DMSO-$d_6$)δ2.41 (s, 3H, pyrrole-CH$_3$), 2.43 (s, 3H, pyrrole-CH$_3$), 3.43 (m, 2H, CH$_2$), 3.48 (m, 2H, CH$_2$), 4.86 (s, 2H, benzene-NH$_2$), 6.56 (m, 2H), 6.76 (d, J=8.0 Hz, 1H), 6.84 (m, 1H), 6.92 (m, 2H), 7.12 (d, J=8.0 Hz, 1H), 7.26 (s 1H), 7.71~7.77 (m, 3H), 7.94 (d,J=8.0 Hz, 1H), 8.65 (s, 1H), 9.38 (s, 1H, benzene-NH), 10.90 (s, 1H, indolinone-NH), 13.69 (s, 1H, pyrrole-NH). LC-MS (m/z) 554 (M+1).

EXAMPLE 4

Preparation of N-(2-aminophenyl)-6-(2-(2-(((5-fluoro-2-oxoindolin-3-ylidene)hydrazono)-methyl)-3,5-dimethyl-1H-pyrrole-4-carboxamido)ethylamino)nicotinamide

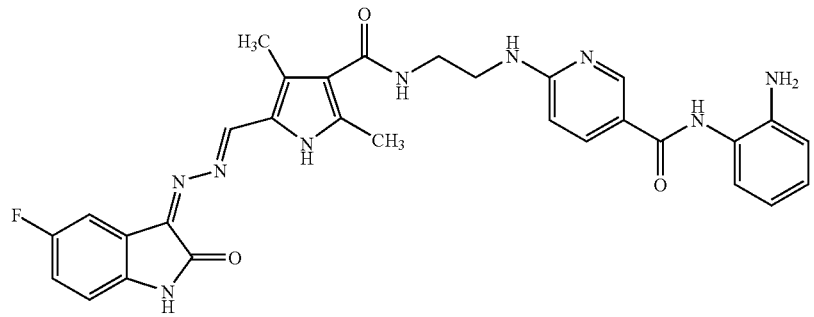

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (425 mg, 73%) as a red solid. $^1$H NMR (DMSO-$d_6$)δ2.35 (s, 3H, pyrrole-CH$_3$), 2.44 (s, 3H, pyrrole-CH$_3$), 3.42 (m, 2H, CH$_2$), 3.48 (m, 2H, CH$_2$), 4.85 (s, 2H, benzene-NH$_2$), 6.56 (m, 2H), 6.76 (d, J=8.0 Hz, 1H), 6.85 (m, 1H), 6.92 (m, 1H), 7.12 (d, J=8.0 Hz, 1H), 7.20~7.25 (m, 2H), 7.71 (s, 1H), 7.93 (d, J=8.0 Hz, 1H), 8.33 (d, J=8.0 Hz, 1H), 8.64 (s, 2H), 9.38 (s, 1H, benzene-NH), 10.73 (s, 1H, indolinone-NH), 11.84 (s, 1H, pyrrole-NH). LC-MS (m/z) 582 (M+1).

EXAMPLE 5

Preparation of N-(2-aminophenyl)-6-(3-aminopropylamino)nicotinamide

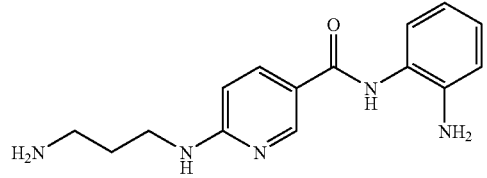

N-(2-Aminophenyl)-6-chloronicotinamide (248 mg, 1 mmol) and 6 ml of 1,3-propanediamine were heated to 80° C. for 3 hours. The excess 1,3-propanediamine was removed under vacuum. To the residue was added 5 ml of 0.20 M NaOH. The mixture was extracted with 100 ml of ethyl acetate. The ethyl acetate was removed under vacuum to give the title compound (168 mg, 59% yield) as a brown solid. LC-MS (m/z) 286 (M+1).

EXAMPLE 6

Preparation of (Z)-N-(2-aminophenyl)-6-(3-(2-((5-fluoro-2-oxoindolin-3-ylidene)methyl)-3,5-dimethyl-1H-pyrrole-4-carboxamido)propylamino)nicotinamide

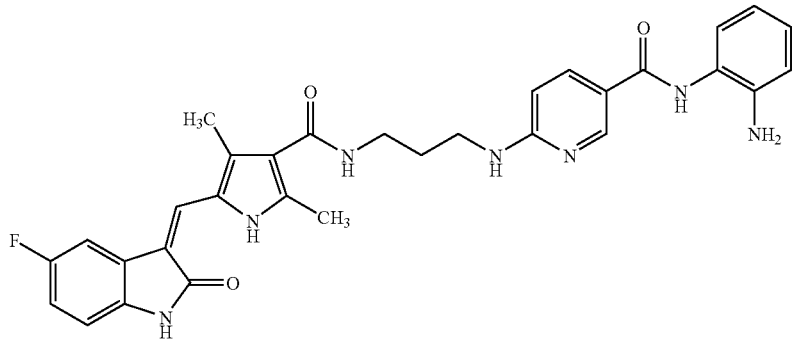

5-(5-Fluoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(3-aminopropylamino)nicotinamide (299 mg, 1.05 mmol) were added. The mixture was stirred for 20 hours at room temperature. The mixture was diluted with 400 mL of brine. The solids were collected by vacuum filtration, washed with water and dried under vacuum to give the title compound (465 mg, 82%) as a yellow solid. $^1$H NMR (DMSO-$d_6$)δ1.79 (m, 2H, CH2), 2.42 (s, 3H, pyrrole-CH$_3$), 2.44 (s, 3H, pyrrole-CH$_3$), 3.30 (m, 2H, CH2), 3.38 (m, 2H, CH2), 4.85 (s, 2H, benzene-NH$_2$), 6.51 (m, 1H), 6.58 (m, 1H), 6.75 (d, J=8.0 Hz, 1H), 6.83 (t, J=8.0 Hz, 1H), 6.92 (m, 2H), 7.12 (d, J=8.0 Hz, 1H), 7.19 (s, 1H), 7.71~7.77 (m, 3H), 7.91 (d, J=8.0 Hz, 1H), 8.64 (s, 1H), 9.37(s, 1H, benzene-NH), 10.90 (s, 1H, indolinone-NH), 13.68 (s, 1H, pyrrole-NH). LC-MS (m/z) 568 (M+1).

EXAMPLE 7

Preparation of N-(2-aminophenyl)-6-(3-(2-(((5-fluoro-2-oxoindolin-3-ylidene)hydrazono)-methyl)-3,5-dimethyl-1H-pyrrole-4-carboxamido)propylamino)nicotinamide

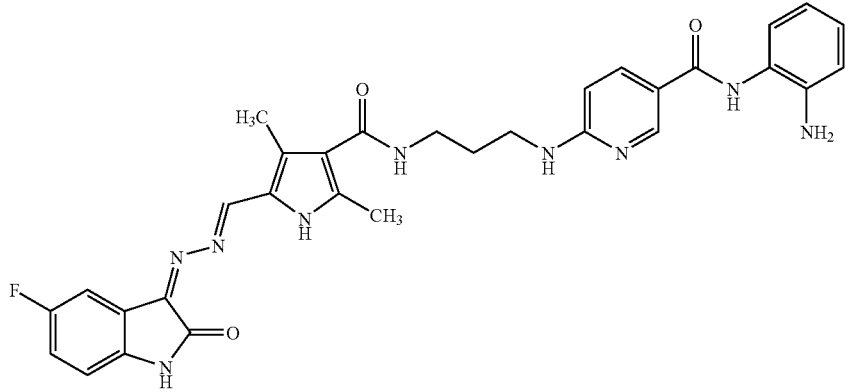

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(3-aminopropylamino)nicotinamide (299 mg, 1.05 mmol) were added. The mixture was stirred for 20 hours at room temperature. The mixture was diluted with 400 mL of brine. The solids were collected by vacuum filtration, washed with water and dried under vacuum to give the title compound (452 mg, 76%) as a red solid. $^1$H NMR (DMSO-$d_6$)δ1.78 (m, 2H, CH$_2$), 2.36 (s, 3H, pyrrole-CH$_3$), 2.45 (s, 3H, pyrrole-CH$_3$), 3.30 (m, 2H, CH$_2$), 3.38 (m, 2H, CH$_2$), 4.85 (s, 2H, benzene-NH$_2$), 6.51 (m, 1H), 6.57 (m, 1H), 6.75 (d, J=8.0 Hz, 1H), 6.85 (m, 1H), 6.93 (m, 1H), 7.12 (d, J=8.0 Hz, 1H), 7.20 (m, 2H), 7.71 (s, 1H), 7.92 (d, J=8.0 Hz, 1H), 8.34 (d, J=8.0 Hz, 1H), 8.64 (s, 2H), 9.37 (s, 1H, benzene-NH), 10.74 (s, 1H, indolinone-NH), 11.85 (s, 1H, pyrrole-NH). LC-MS (m/z) 596 (M+1).

EXAMPLE 8

Preparation of N-(2-aminophenyl)-6-(4-aminobutylamino)nicotinamide

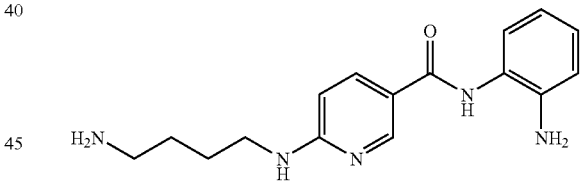

N-(2-Aminophenyl)-6-chloronicotinamide (248 mg, 1 mmol) and 7 ml of 1,4-butanediamine were heated to 80° C. for 3 hours. The excess 1,4-butanediamine was removed under vacuum. To the residue was added 5 ml of 0.20 M NaOH. The mixture was extracted with 100 ml of ethyl acetate. The ethyl acetate was removed under vacuum to give the title compound (158 mg, 53% yield) as a brown solid. LC-MS (m/z) 300 (M+1).

EXAMPLE 9

Preparation of (Z)-N-(2-aminophenyl)-6-(4-(2-((5-fluoro-2-oxoindolin-3-ylidene)methyl)-3,5-dimethyl-1H-pyrrole-4-carboxamido)butylamino)nicotinamide

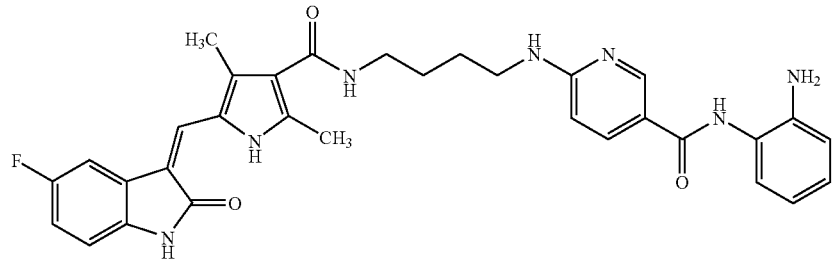

5-(5-Fluoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(4-aminobutylamino)nicotinamide (314 mg, 1.05 mmol) were added. The mixture was stirred for 20 hours at room temperature. The mixture was diluted with 400 mL of brine. The solids were collected by vacuum filtration, washed with water and dried under vacuum to give the title compound (447 mg, 77%) as a yellow solid. $^1$H NMR (DMSO-$d_6$)δ1.59 (m, 4H, $CH_2CH_2$), 2.39 (s, 3H, pyrrole-$CH_3$), 2.41 (s, 3H, pyrrole-$CH_3$), 3.25 (m, 4H, 2×$CH_2$), 4.85 (s, 2H, benzene-$NH_2$), 6.49 (m, 1H), 6.57 (m, 1H), 6.75 (d, J=8.0 Hz, 1H), 6.83 (m, 1H), 6.91 (m, 2H), 7.12 (d, J=8.0 Hz, 1H), 7.18 (s, 1H), 7.67~7.76 (m, 3H), 7.90 (d, J=8.0 Hz, 1H), 8.63 (s, 1H), 9.35 (s, 1H, benzene-NH), 10.88 (s, 1H, indolinone-NH), 13.66 (s, 1H, pyrrole-NH). LC-MS (m/z) 582 (M+1).

EXAMPLE 10

Preparation of N-(2-aminophenyl)-6-(4-(2-(((5-fluoro-2-oxoindolin-3-ylidene)hydrazono)-methyl)-3,5-dimethyl-1H-pyrrole-4-carboxamido)butylamino)nicotinamide

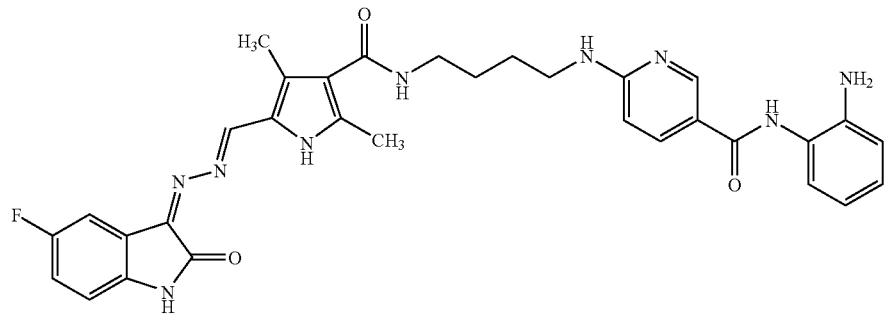

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(4-aminobutylamino)nicotinamide (314 mg, 1.05 mmol) were added. The mixture was stirred for 20 hours at room temperature. The mixture was diluted with 400 mL of brine. The solids were collected by vacuum filtration, washed with water and dried under vacuum to give the title compound (444 mg, 73%) as a red solid. $^1$H NMR (DMSO-$d_6$)δ1.59 (m, 4H, $CH_2CH_2$), 2.32 (s, 3H, pyrrole-$CH_3$), 2.43 (s, 3H, pyrrole-$CH_3$), 3.24 (m, 4H, 2×$CH_2$), 4.85 (s, 2H, benzene-$NH_2$), 6.49 (m, 1H), 6.57 (m, 1H), 6.76 (d, J=8.0 Hz, 1H), 6.85 (m, 1H), 6.93 (m, 1H), 7.12 (d, J=8.0 Hz, 1H), 7.20 (m, 2H), 7.67 (s, 1H), 7.89 (d, J=8.0 Hz, 1H), 8.33 (d, J=8.0 Hz, 1H), 8.63 (s, 2H), 9.35 (s, 1H, benzene-NH), 10.70 (s, 1H, indolinone-NH), 11.82 (s, 1H, pyrrole-NH). LC-MS (m/z) 610 (M+1).

EXAMPLE 11

Preparation of N-(2-amino-4-fluorophenyl)-6-chloronicotinamide

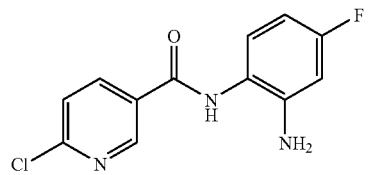

6-Chloronicotinic acid (157.5 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and 4-fluoro-o-phenylenediamine (151 mg, 1.2 mmol) were added. The mixture was stirred for 20 hours at room temperature. The mixture was diluted with 400 mL of brine and extracted with 200 ml of ethyl acetate. The ethyl acetate was removed under vacuum. To the residue was added 5 ml of absolute ethanol. The solids were collected by vacuum filtration, washed with absolute ethanol and dried under vacuum to give the title compound (193 mg, 73% yield) as a brown solid. LC-MS (m/z) 266 (M+1).

EXAMPLE 12

Preparation of N-(2-amino-4-fluorophenyl)-6-(2-aminoethylamino)nicotinamide

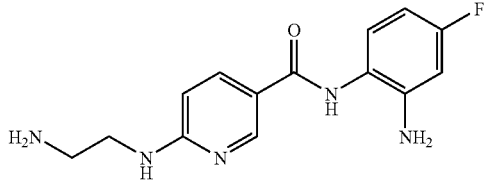

-(2-Amino-4-fluorophenyl)-6-chloronicotinamide (266 mg, 1 mmol) and 5 ml of ethylenediamine were heated to 80° C. for 3 hours. The excess ethylenediamine was removed under vacuum. To the residue was added 5 ml of 0.20 M NaOH. The mixture was extracted with 100 ml of ethyl acetate. The ethyl acetate was removed under vacuum to give the title compound (176 mg, 61% yield) as a brown solid. LC-MS (m/z) 290 (M+1).

EXAMPLE 13

Preparation of (Z)-N-(2-amino-4-fluorophenyl)-6-(2-(2-(((5-fluoro-2-oxoindolin-3-ylidene)-methyl)-3,5-dimethyl-1H-pyrrole-4-carboxamido)ethylamino)nicotinamide

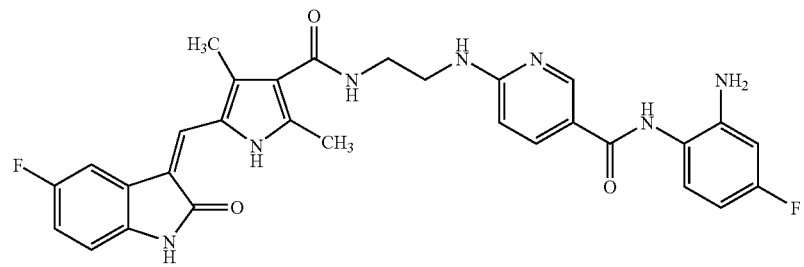

5-(5-Fluoro-2-oxo-1,2-dihydro-indol-(3Z)-ylidenem-ethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-fluorophenyl)-6-(2-aminoethylamino)nicotinamide (303 mg, 1.05 mmol) were added. The mixture was stirred for 20 hours at room temperature. The mixture was diluted with 400 mL of brine. The solids were collected by vacuum filtration, washed with water and dried under vacuum to give the title compound (457 mg, 80%) as a yellow solid. $^1$H NMR (DMSO-$d_6$)δ2.41 (s, 3H, pyrrole-CH$_3$), 2.43 (s, 3H, pyrrole-CH$_3$), 3.43 (m, 2H, CH$_2$), 3.48 (m, 2H, CH$_2$), 5.18 (s, 2H, benzene-NH$_2$), 6.33 (m, 1H), 6.53 (m, 2H), 6.84 (m, 1H), 6.91 (m, 1H), 7.07 (m, 1H), 7.25 (s, 1H), 7.71 (m, 3H), 7.92 (d, J=8.0 Hz, 1H), 8.64 (s, 1H), 9.31 (s, 1H, benzene-NH), 10.89 (s, 1H, indolinone-NH), 13.68 (s, 1H, pyrrole-NH). LC-MS (m/z) 572 (M+1).

EXAMPLE 14

Preparation of N-(2-amino-4-fluorophenyl)-6-(2-(2-(((5-fluoro-2-oxoindolin-3-ylidene)-hydrazono)me-thyl)-3,5-dimethyl-1H-pyrrole-4-carboxamido)ethy-lamino)nicotinamide

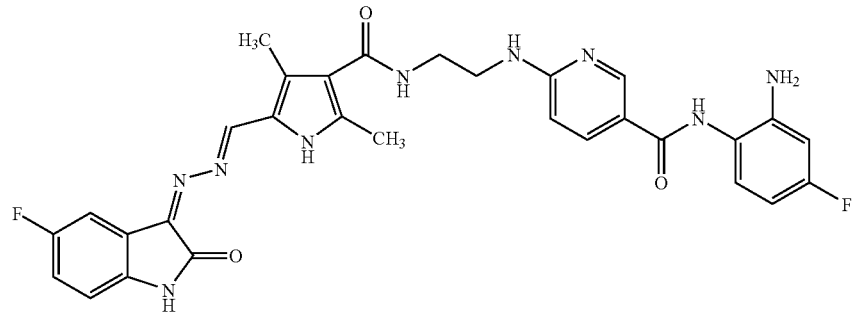

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-fluorophenyl)-6-(2-aminoethylamino)nicotinamide (303 mg, 1.05 mmol) were added. The mixture was stirred for 20 hours at room temperature. The mixture was diluted with 400 mL of brine. The solids were collected by vacuum filtration, washed with water and dried under vacuum to give the title compound (407 mg, 68%) as a red solid. $^1$H NMR (DMSO-$d_6$)δ2.35 (s, 3H, pyrrole-CH$_3$), 2.44 (s, 3H, pyrrole-CH$_3$), 3.42 (m, 2H, CH$_2$), 3.47 (m, 2H, CH$_2$), 5.18 (s, 2H, benzene-NH$_2$), 6.33 (m, 1H), 6.53 (m, 2H), 6.85 (m, 1H), 7.06 (m, 1H), 7.21~7.25 (m, 2H), 7.71 (s, 1H), 7.93 (d, J=8.0 Hz, 1H), 8.33 (d, J=8.0 Hz, 1H), 8.64 (s, 2H) 9.31 (s, 1H, benzene-NH), 10.73 (s, 1H, indolinone-NH), 11.84 (s, 1H, pyrrole-NH). LC-MS (m/z) 600 (M+1).

5-(5-Fluoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-fluorophenyl)-6-(3-aminopropylamino)nicotinamide (318 mg, 1.05 mmol) were added. The mixture was stirred for 20 hours at room temperature. The mixture was diluted with 400 mL of brine. The solids were collected by vacuum filtration, washed with water and dried under vacuum to give the title compound (456 mg, 78%) as a yellow solid. $^1$H NMR (DMSO-$d_6$)δ 1.78 (m, 2H, CH$_2$), 2.42 (s, 3H, pyrrole-CH$_3$), 2.44 (s, 3H, pyrrole-CH$_3$), 3.30 (m, 2H, CH$_2$), 3.38 (m, 2H, CH$_2$), 5.18 (s, 2H, benzene-NH$_2$), 6.33 (m, 1H), 6.51 (m, 2H), 6.84 (m, 1H), 6.90 (m, 1H), 7.06 (t, J=8.0 Hz, 1H), 7.20 (s, 1H), 7.71~7.76 (m, 3H), 7.91 (d, J=8.0 Hz, 1H), 8.63 (s, 1H), 9.30 (s, 1H, benzene-NH), 10.90 (s, 1H, indolinone-NH), 13.68 (s, 1H, pyrrole-NH). LC-MS (m/z) 586 (M+1).

EXAMPLE 15

Preparation of N-(2-amino-4-fluorophenyl)-6-(3-aminopropylamino)nicotinamide

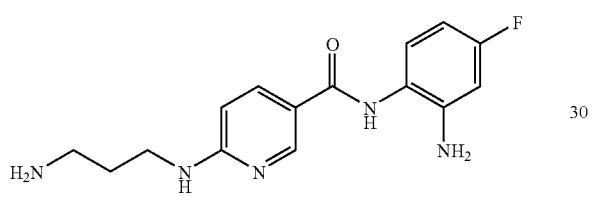

N-(2-amino-4-fluorophenyl)-6-chloronicotinamide (266 mg, 1 mmol) and 6 ml of 1,3-propanediamine were heated to 80° C. for 3 hours. The excess 1,3-propanediamine was removed under vacuum. To the residue was added 5 ml of 0.20 M NaOH. The mixture was extracted with 100 ml of ethyl acetate. The ethyl acetate was removed under vacuum to give the title compound (158 mg, 52% yield) as a brown solid. LC-MS (m/z) 304 (M+1).

EXAMPLE 16

Preparation of (Z)-N-(2-amino-4-fluorophenyl)-6-(3-(2-((5-fluoro-2-oxoindolin-3-ylidene)-methyl)-3,5-dimethyl-1H-pyrrole-4-carboxamido)propylamino)nicotinamide

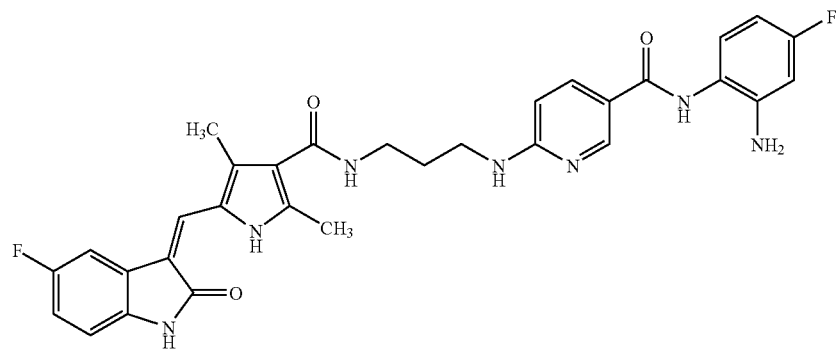

EXAMPLE 17

Preparation of N-(2-amino-4-fluorophenyl)-6-(3-(2-(((5-fluoro-2-oxoindolin-3-ylidene)-hydrazono)methyl)-3,5-dimethyl-1H-pyrrole-4-carboxamido)propylamino)nicotinamide

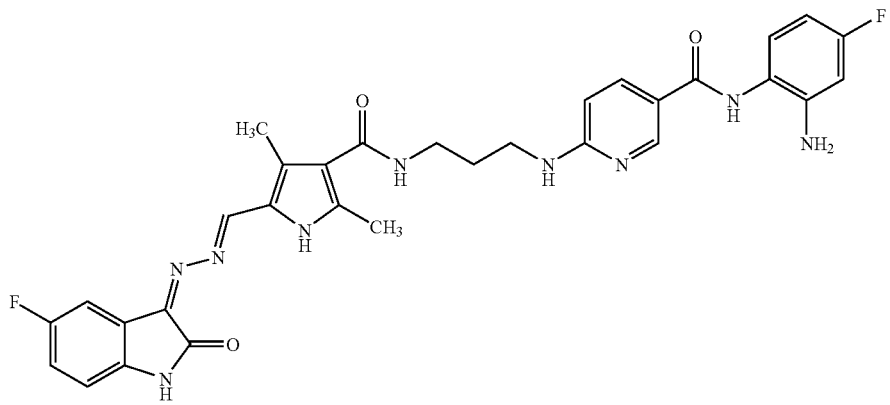

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-fluorophenyl)-6-(3-aminopropylamino)nicotinamide (318 mg, 1.05 mmol) were added. The mixture was stirred for 20 hours at room temperature. The mixture was diluted with 400 mL of brine. The solids were collected by vacuum filtration, washed with water and dried under vacuum to give the title compound (441 mg, 72%) as a red solid. $^1$H NMR (DMSO-d$_6$)δ1.77 (m, 2H, CH$_2$), 2.36 (s, 3H, pyrrole-CH$_3$), 2.45 (s, 3H, pyrrole-CH$_3$), 3.29 (m, 2H, CH$_2$), 3.38 (m, 2H, CH$_2$), 5.18 (s, 2H, benzene-NH$_2$), 6.32 (m, 1H), 6.51 (m, 2H), 6.85 (m, 1H), 7.06 (m, 1H), 7.20 (m, 2H), 7.71 (s, 1H), 7.90 (d, J=8.0 Hz, 1H), 8.33 (d, J=8.0 Hz, 1H), 8.64 (s, 2H), 9.29 (s, 1H, benzene-NH), 10.73 (s, 1H, indolinone-NH), 11.84 (s, 1H, pyrrole-NH). LC-MS (m/z) 614 (M+1).

EXAMPLE 18

Preparation of N-(2-amino-4-fluorophenyl)-6-(4-aminobutylamino)nicotinamide

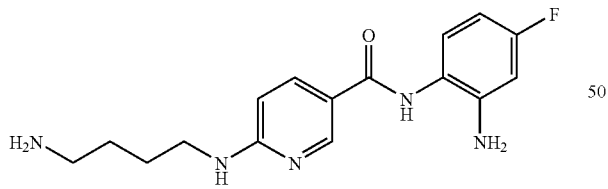

N-(2-Amino-4-fluorophenyl)-6-chloronicotinamide (266 mg, 1 mmol) and 7 ml of 1,4-butanediamine were heated to 80° C. for 3 hours. The excess 1,4-butanediamine was removed under vacuum. To the residue was added 5 ml of 0.20 M NaOH. The mixture was extracted with 100 ml of ethyl acetate. The ethyl acetate was removed under vacuum to give the title compound (149 mg, 47% yield) as a brown solid. LC-MS (m/z) 318 (M+1).

EXAMPLE 19

Preparation of (Z)-N-(2-amino-4-fluorophenyl)-6-(4-(2-((5-fluoro-2-oxoindolin-3-ylidene)-methyl)-3,5-dimethyl-1H-pyrrole-4-carboxamido)butylamino)nicotinamide

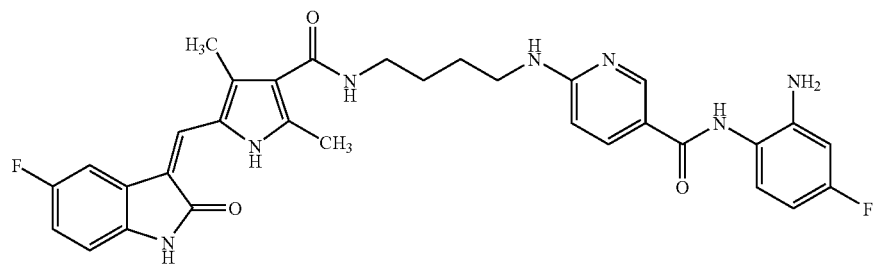

5-(5-Fluoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-fluorophenyl)-6-(4-aminobutylamino)nicotinamide (333 mg, 1.05 mmol) were added. The mixture was stirred for 20 hours at room temperature. The mixture was diluted with 400 mL of brine. The solids were collected by vacuum filtration, washed with water and dried under vacuum to give the title compound (485 mg, 81%) as a yellow solid.
$^1$H NMR (DMSO-$d_6$) δ 1.59 (m, 4H, CH$_2$CH$_2$), 2.39 (s, 3H, pyrrole-CH$_3$), 2.41 (s, 3H, pyrrole-CH$_3$), 3.24 (m, 2H, CH$_2$), 3.34 (m, 2H, CH$_2$), 5.17 (s, 2H, benzene-NH$_2$), 6.33 (m, 1H), 6.50 (m, 2H), 6.83 (m, 1H), 6.91 (m, 1H), 7.06 (t, J=8.0 Hz, 1H), 7.18 (s, 1H), 7.67~7.76 (m, 3H), 7.89 (d, J=8.0 Hz, 1H), 8.63 (s, 1H), 9.28 (s, 1H, benzene-NH), 10.89 (s, 1H, indolinone-NH), 13.67 (s, 1H, pyrrole-NH). LC-MS (m/z) 600 (M+1).

EXAMPLE 20

Preparation of N-(2-amino-4-fluorophenyl)-6-(4-(2-(((5-fluoro-2-oxoindolin-3-ylidene)-hydrazono)methyl)-3,5-dimethyl-1H-pyrrole-4-carboxamido)butylamino)nicotinamide

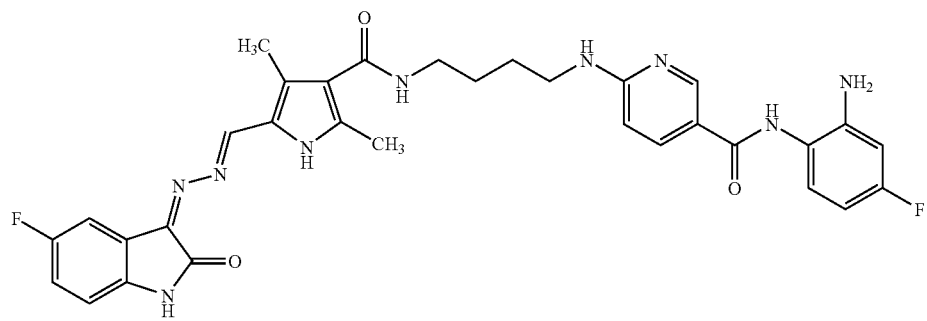

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-fluorophenyl)-6-(4-aminobutylamino)nicotinamide (333 mg, 1.05 mmol) were added. The mixture was stirred for 20 hours at room temperature. The mixture was diluted with 400 mL of brine. The solids were collected by vacuum filtration, washed with water and dried under vacuum to give the title compound (433 mg, 69%) as a red solid. $^1$H NMR (DMSO-$d_6$) δ 1.58 (m, 4H, CH$_2$CH$_2$), 2.32 (s, 3H, pyrrole-CH$_3$), 2.42 (s, 3H, pyrrole-CH$_3$), 3.24 (m, 2H, CH$_2$), 3.35 (m, 2H, CH$_2$), 5.18 (s, 2H, benzene-NH$_2$), 6.33 (m, 1H), 6.50 (m, 2H), 6.85 (m, 1H), 7.06 (m, 1H), 7.20 (m, 2H), 7.67 (s, 1H), 7.89 (d, J=8.0 Hz, 1H), 8.33 (d, J=8.0 Hz, 1H), 8.63 (s, 2H), 9.29 (s, 1H, benzene-NH), 10.74 (s, 1H, indolinone-NH), 11.83 (s, 1H, pyrrole-NH). LC-MS (m/z) 628 (M+1).

EXAMPLE 21

Preparation of N-(2-amino-4-chlorophenyl)-6-chloronicotinamide

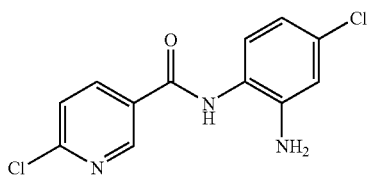

6-Chloronicotinic acid (157.5 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and 4-chloro-o-phenylenediamine (171 mg, 1.2 mmol) were added. The mixture was stirred for 20 hours at room temperature. The mixture was diluted with 400 mL of brine and extracted with 200 ml of ethyl acetate. The ethyl acetate was removed under vacuum. To the residue was added 5 ml of absolute ethanol. The solids were collected by vacuum filtration, washed with absolute ethanol and dried under vacuum to give the title compound (135 mg, 48% yield) as a brown solid. LC-MS (m/z) 282 (M+1).

EXAMPLE 22

Preparation of N-(2-amino-4-chlorophenyl)-6-(2-aminoethylamino)nicotinamide

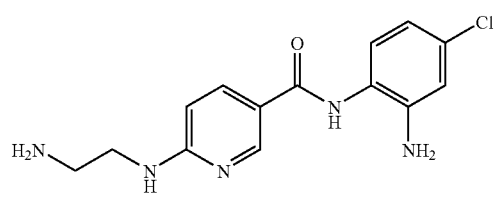

N-(2-Amino-4-chlorophenyl)-6-chloronicotinamide (282 mg, 1 mmol) and 5 ml of ethylenediamine were heated to 80° C. for 3 hours. The excess ethylenediamine was removed under vacuum. To the residue was added 5 ml of 0.20 M NaOH. The mixture was extracted with 100 ml of ethyl acetate. The ethyl acetate was removed under vacuum to give the title compound (180 mg, 59% yield) as a brown solid. LC-MS (m/z) 306 (M+1).

EXAMPLE 23

Preparation of (Z)-N-(2-amino-4-chlorophenyl)-6-(2-(2-((5-fluoro-2-oxoindolin-3-ylidene)-methyl)-3,5-dimethyl-1H-pyrrole-4-carboxamido)ethylamino)nicotinamide

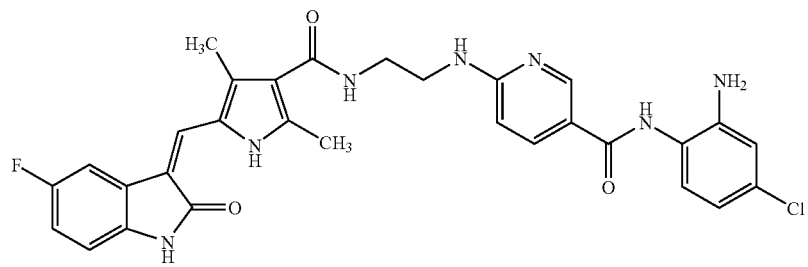

5-(5-Fluoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-chlorophenyl)-6-(2-aminoethylamino)nicotinamide (321 mg, 1.05 mmol) were added. The mixture was stirred for 20 hours at room temperature. The mixture was diluted with 400 mL of brine. The solids were collected by vacuum filtration, washed with water and dried under vacuum to give the title compound (446 mg, 76%) as a yellow solid. LC-MS (m/z) 588 (M+1).

EXAMPLE 24

Preparation of N-(2-amino-4-chlorophenyl)-6-(2-(2-(((5-fluoro-2-oxoindolin-3-ylidene)-hydrazono)methyl)-3,5-dimethyl-1H-pyrrole-4-carboxamido)ethylamino)nicotinamide

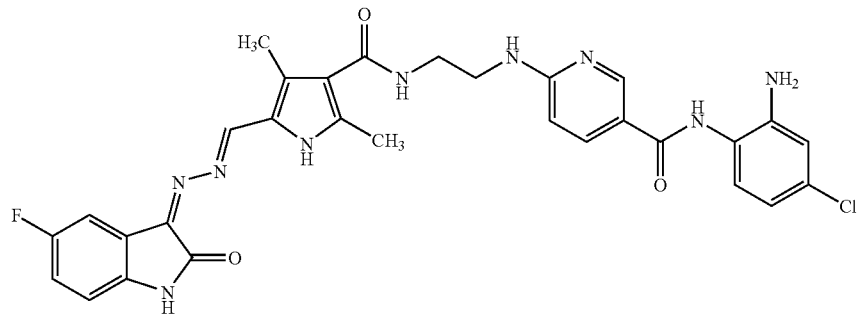

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-chlorophenyl)-6-(2-aminoethylamino)nicotinamide (321 mg, 1.05 mmol) were added. The mixture was stirred for 20 hours at room temperature. The mixture was diluted with 400 mL of brine. The solids were collected by vacuum filtration, washed with water and dried under vacuum to give the title compound (406 mg, 66%) as a red solid. LC-MS (m/z) 616 (M+1).

EXAMPLE 25

Preparation of N-(2-amin-4-methylophenyl)-6-chloronicotinamide

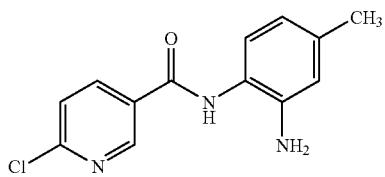

6-Chloronicotinic acid (157.5 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and 4-methyl-o-phenylenediamine (146 mg, 1.2 mmol) were added. The mixture was stirred for 20 hours at room temperature. The mixture was diluted with 400 mL of brine and extracted with 200 ml of ethyl acetate. The ethyl acetate was removed under vacuum. To the residue was added 5 ml of absolute ethanol. The solids were collected by vacuum filtration, washed with absolute ethanol and dried under vacuum to give the title compound (164 mg, 63% yield) as a brown solid. LC-MS (m/z) 262 (M+1).

EXAMPLE 26

Preparation of N-(2-amino-4-methylphenyl)-6-(2-aminoethylamino)nicotinamide

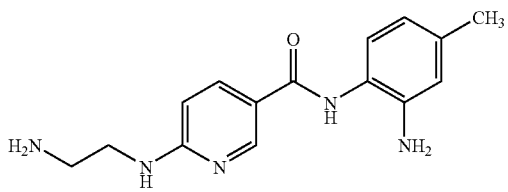

N-(2-Amino-4-methyl-phenyl)-6-chloronicotinamide (261 mg, 1 mmol) and 5 ml of ethylenediamine were heated to 80° C. for 3 hours. The excess ethylenediamine was removed under vacuum. To the residue was added 5 ml of 0.20 M NaOH. The mixture was extracted with 100 ml of ethyl acetate. The ethyl acetate was removed under vacuum to give the title compound (145 mg, 51% yield) as a brown solid. LC-MS (m/z) 286 (M+1).

EXAMPLE 27

Preparation of (Z)-N-(2-amino-4-methylphenyl)-6-(2-(2-((5-fluoro-2-oxoindolin-3-ylidene)-methyl)-3,5-dimethyl-1H-pyrrole-4-carboxamido)ethylamino)nicotinamide

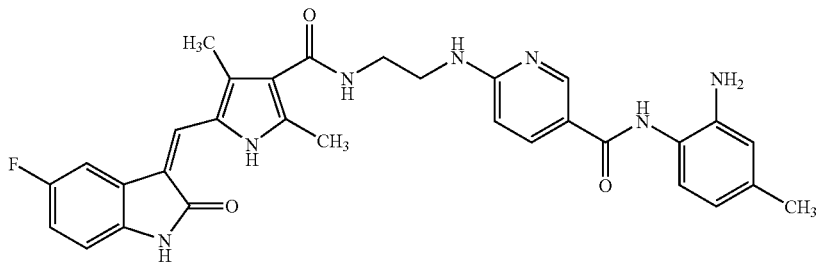

5-(5-Fluoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-methylphenyl)-6-(2-aminoethylamino)nicotinamide (299 mg, 1.05 mmol) were added. The mixture was stirred for 20 hours at room temperature. The mixture was diluted with 400 mL of brine. The solids were collected by vacuum filtration, washed with water and dried under vacuum to give the title compound (420 mg, 74%) as a yellow solid. LC-MS (m/z) 568 (M+1).

EXAMPLE 28

Preparation of N-(2-amino-4-methylphenyl)-6-(2-(2-(((5-fluoro-2-oxoindolin-3-ylidene)-hydrazono)methyl)-3,5-dimethyl-1H-pyrrole-4-carboxamido)ethylamino)nicotinamide

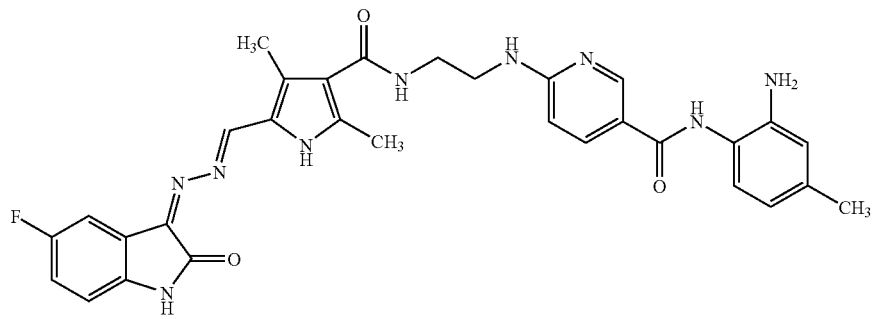

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-methylphenyl)-6-(2-aminoethylamino)nicotinamide (299 mg, 1.05 mmol) were added. The mixture was stirred for 20 hours at room temperature. The mixture was diluted with 400 mL of brine. The solids were collected by vacuum filtration, washed with water and dried under vacuum to give the title compound (363 mg, 61%) as a red solid. LC-MS (m/z) 596 (M+1).

EXAMPLE 29

Preparation of N-(2-amino-4-methoxyphenyl)-6-chloronicotinamide

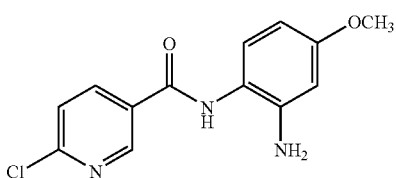

6-Chloronicotinic acid (157.5 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and 4-methoxy-o-phenylenediamine (166 mg, 1.2 mmol) were added. The mixture was stirred for 20 hours at room temperature. The mixture was diluted with 400 mL of brine and extracted with 200 ml of ethyl acetate. The ethyl acetate was removed under vacuum. To the residue was added 5 ml of absolute ethanol. The solids were collected by vacuum filtration, washed with absolute ethanol and dried under vacuum to give the title compound (144 mg, 52% yield) as a brown solid. LC-MS (m/z) 278 (M+1).

EXAMPLE 30

Preparation of N-(2-amino-4-methoxyphenyl)-6-(2-aminoethylamino)nicotinamide

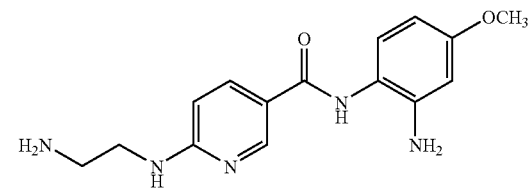

N-(2-Amino-4-methoxyphenyl)-6-chloronicotinamide (277 mg, 1 mmol) and 5 ml of ethylenediamine were heated to 80° C. for 3 hours. The excess ethylenediamine was removed under vacuum. To the residue was added 5 ml of 0.20 M NaOH. The mixture was extracted with 100 ml of ethyl acetate. The ethyl acetate was removed under vacuum to give the title compound (144 mg, 48% yield) as a brown solid. LC-MS (m/z) 302 (M+1).

EXAMPLE 31

Preparation of (Z)-N-(2-amino-4-methoxyphenyl)-6-(2-(2-((5-fluoro-2-oxoindolin-3-ylidene)-methyl)-3,5-dimethyl-1H-pyrrole-4-carboxamido)ethylamino)nicotinamide

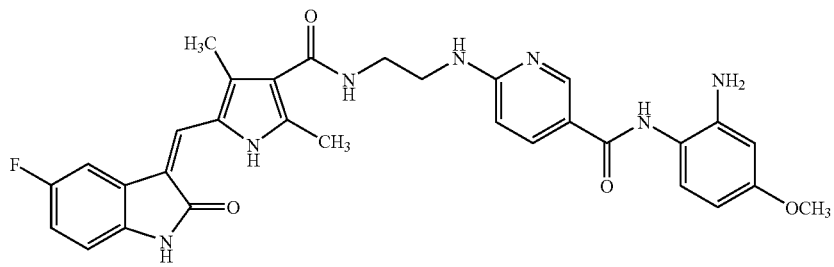

5-(5-fFuoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-methoxyphenyl)-6-(2-aminoethylamino)nicotinamide (316 mg, 1.05 mmol) were added. The mixture was stirred for 20 hours at room temperature. The mixture was diluted with 400 mL of brine. The solids were collected by vacuum filtration, washed with water and dried under vacuum to give the title compound (478 mg, 82%) as a yellow solid. LC-MS (m/z) 584 (M+1).

EXAMPLE 32

Preparation of N-(2-amino-4-methoxyphenyl)-6-(2-(2-(((5-fluoro-2-oxoindolin-3-ylidene)hydrazono)-methyl)-3,5-dimethyl-1H-pyrrole-4-carboxamido) ethylamino)nicotinamide

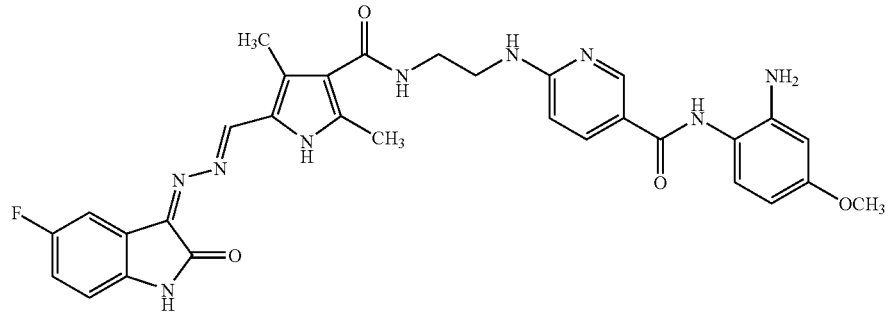

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-methoxyphenyl)-6-(2-aminoethylamino)nicotinamide (316 mg, 1.05 mmol) were added. The mixture was stirred for 20 hours at room temperature. The mixture was diluted with 400 mL of brine. The solids were collected by vacuum filtration, washed with water and dried under vacuum to give the title compound (397 mg, 65%) as a red solid. LC-MS (m/z) 612 (M+1).

EXAMPLE 33

Preparation of N-(2-amino-4-trifluoromethylphenyl)-6-chloronicotinamide

6-Chloronicotinic acid (157.5 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and 4-trifluoromethyl-o-phenylenediamine (211 mg, 1.2 mmol) were added. The mixture was stirred for 20 hours at room temperature. The mixture was diluted with 400 mL of brine and extracted with 200 ml of ethyl acetate. The ethyl acetate was removed under vacuum. To the residue was added 5 ml of absolute ethanol. The solids were collected by vacuum filtration, washed with absolute ethanol and dried under vacuum to give the title compound (418 mg, 42% yield) as a brown solid. LC-MS (m/z) 316 (M+1).

EXAMPLE 34

Preparation of N-(2-amino-4-trifluoromethylphenyl)-6-(2-aminoethylamino)nicotinamide

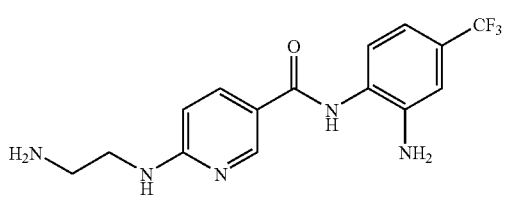

N-(2-Amino-4-trifluoromethylphenyl)-6-chloronicotinamide (316 mg, 1 mmol) and 5 ml of ethylenediamine were heated to 80° C. for 3 hours. The excess ethylenediamine was removed under vacuum. To the residue was added 5 ml of 0.20 M NaOH. The mixture was extracted with 100 ml of ethyl acetate. The ethyl acetate was removed under vacuum to give the title compound (159 mg, 47% yield) as a brown solid. LC-MS (m/z) 340 (M+1).

EXAMPLE 35

Preparation of (Z)-N-(2-amino-4-trifluoromethylphenyl)-6-(2-(2-((5-fluoro-2-oxoindolin-3-ylidene)methyl)-3,5-dimethyl-1H-pyrrole-4-carboxamido)ethylamino)nicotinamide

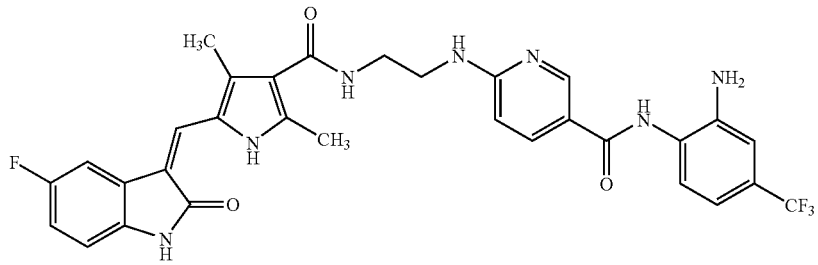

5-(5-Fluoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-trifluoromethylphenyl)-6-(2-aminoethylamino) nicotinamide (356 mg, 1.05 mmol) were added. The mixture was stirred for 20 hours at room temperature. The mixture was diluted with 400 mL of brine. The solids were collected by vacuum filtration, washed with water and dried under vacuum to give the title compound (422 mg, 68%) as a yellow solid. LC-MS (m/z) 622 (M+1).

EXAMPLE 36

Preparation of N-(2-amino-4-trifluoromethylphenyl)-6-(2-(2-(((5-fluoro-2-oxoindolin-3-ylidene)-hydrazono)methyl)-3,5-dimethyl-1H-pyrrole-4-carboxamido)ethylamino)nicotinamide

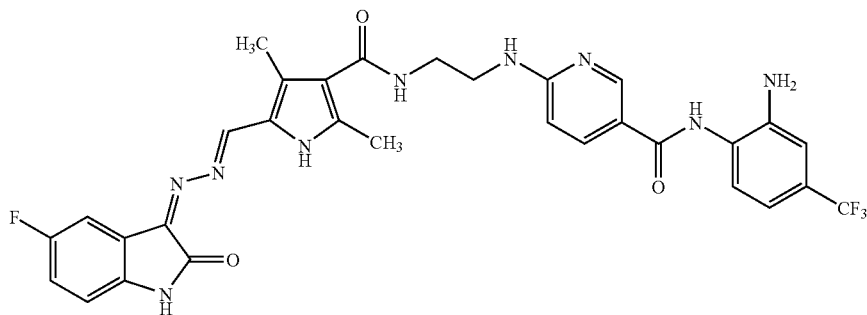

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-amino-4-trifluorophenyl)-6-(2-aminoethylamino)nicotinamide (356 mg, 1.05 mmol) were added. The mixture was stirred for 20 hours at room temperature. The mixture was diluted with 400 mL of brine. The solids were collected by vacuum filtration, washed with water and dried under vacuum to give the title compound (350 mg, 54%) as a red solid. LC-MS (m/z) 650 (M+1).

EXAMPLE 37

Preparation of (Z)-N-(2-aminophenyl)-6-(2-(2-((2-oxoindolin-3-ylidene)methyl)-3,5-dimethyl-1H-pyrrole-4-carboxamido)ethylamino)nicotinamide

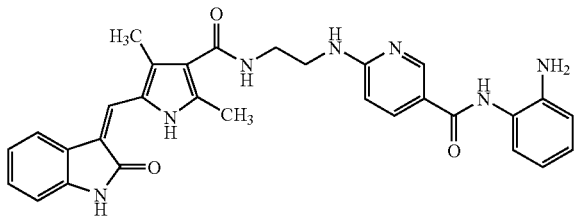

5-(2-Oxo-1,2-dihydro-indol-(3Z)-ylidenemethyl)-2,4-dimethyl-1H-pyrrole-3-carboxylic acid (282 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (460 mg, 86%) as a yellow solid. LC-MS (m/z) 536 (M+1).

EXAMPLE 38

Preparation of N-(2-aminophenyl)-6-(2-(2-(((2-oxoindolin-3-ylidene)hydrazono)-methyl)-3,5-dimethyl-1H-pyrrole-4-carboxamido)ethylamino)nicotinamide

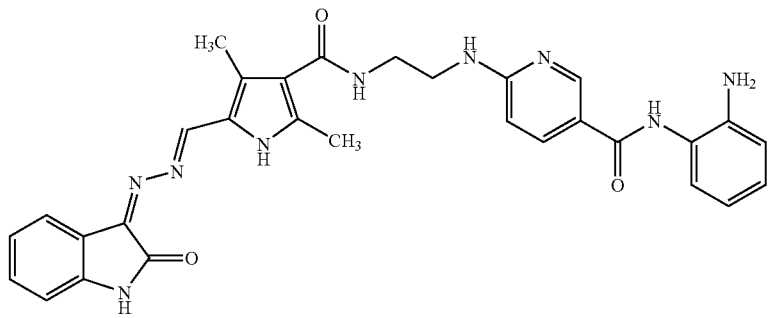

2-(((2-Oxoindolin-3-ylidene)hydrazono)methyl)-2,4-dimethyl-1H-pyrrole-4-carboxylic acid (310 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (394 mg, 70%) as a red solid. LC-MS (m/z) 564 (M+1).

EXAMPLE 39

Preparation of (Z)-N-(2-aminophenyl)-6-(2-(2-((5-chloro-2-oxoindolin-3-ylidene)methyl)-3,5-dimethyl-1H-pyrrole-4-carboxamido)ethylamino)nicotinamide

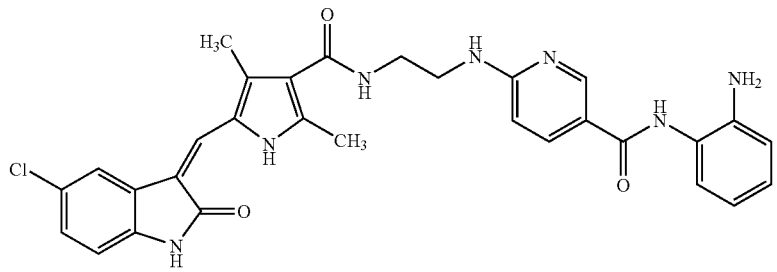

5-(5-Chloro-2-oxo-1,2-dihydro-indol-(3Z)-ylidenemethyl)-2,4-dimethyl-1H-pyrrole-3-carboxylic acid (316 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (444 mg, 77%) as a yellow solid. LC-MS (m/z) 570 (M+1).

EXAMPLE 40

Preparation of N-(2-aminophenyl)-6-(2-(2-(((5-chloro-2-oxoindolin-3-ylidene)hydrazono)-methyl)-3,5-dimethyl-1H-pyrrole-4-carboxamido)ethylamino)nicotinamide

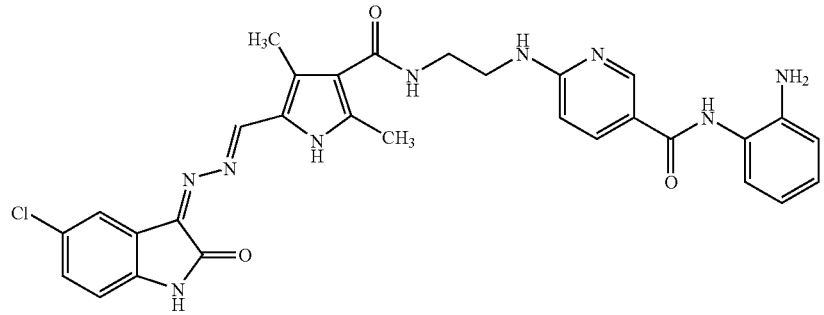

2-(((5-Chloro-2-oxoindolin-3-ylidene)hydrazono)methyl)-2,4-dimethyl-1H-pyrrole-4-carboxylic acid (344 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (376 mg, 63%) as a red solid. LC-MS (m/z) 598 (M+1).

EXAMPLE 41

Preparation of (Z)-N-(2-aminophenyl)-6-(2-(2-((4-methyl-2-oxoindolin-3-ylidene)methyl)-3,5-dimethyl-1H-pyrrole-4-carboxamido)ethylamino)nicotinamide

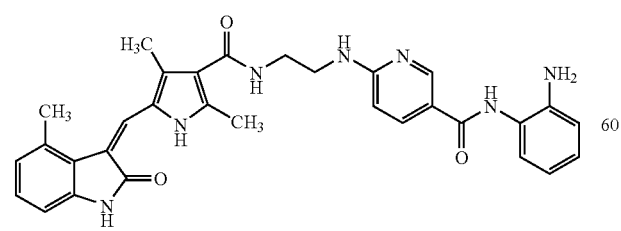

5-(4-Methyl-2-oxo-1,2-dihydro-indol-(3Z)-ylidenemethyl)-2,4-dimethyl-1H-pyrrole-3-carboxylic acid (296 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (445 mg, 81%) as a yellow solid. LC-MS (m/z) 550 (M+1).

EXAMPLE 42

Preparation of N-(2-aminophenyl)-6-(2-(2-(((4-methyl-2-oxoindolin-3-ylidene)hydrazono)-methyl)-3,5-dimethyl-1H-pyrrole-4-carboxamido)ethylamino)nicotinamide

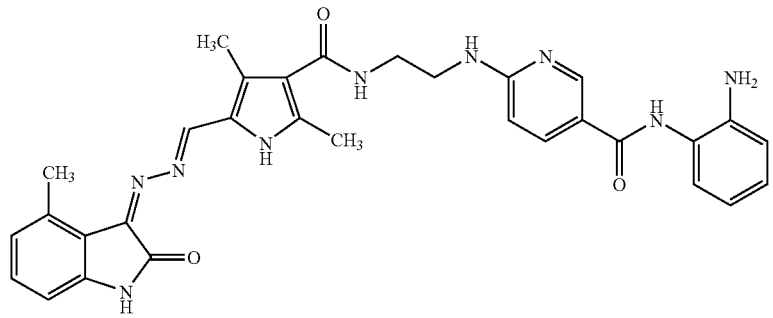

2-(((4-Methyl-2-oxoindolin-3-ylidene)hydrazono)methyl)-2,4-dimethyl-1H-pyrrole-4-carboxylic acid (324 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (438 mg, 76%) as a red solid. LC-MS (m/z) 578 (M+1).

EXAMPLE 43

Preparation of (Z)-N-(2-aminophenyl)-6-(2-(2-((5-nitro-2-oxoindolin-3-ylidene)methyl)-3,5-dimethyl-1H-pyrrole-4-carboxamido)ethylamino)nicotinamide

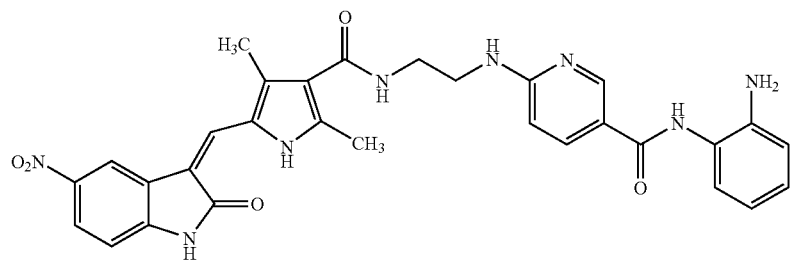

5-(5-Nitro-2-oxo-1,2-dihydro-indol-(3Z)-ylidenemethyl)-2,4-dimethyl-1H-pyrrole-3-carboxylic acid (327 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (383 mg, 66%) as a yellow solid. LC-MS (m/z) 581 (M+1).

EXAMPLE 44

Preparation of N-(2-aminophenyl)-6-(2-(2-((((5-nitro-2-oxoindolin-3-ylidene)hydrazono)-methyl)-3,5-dimethyl-1H-pyrrole-4-carboxamido)ethylamino)nicotinamide

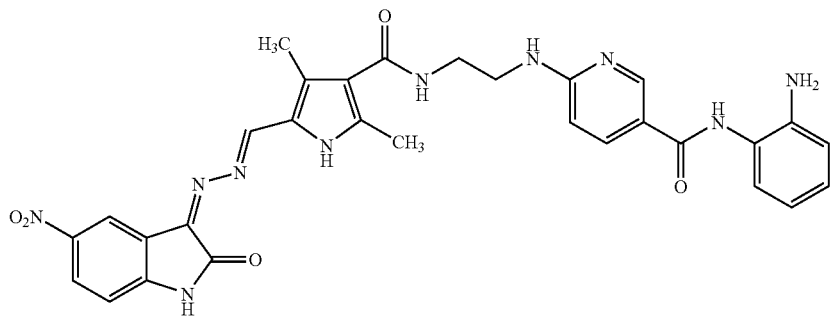

2-(((5-Nitro-2-oxoindolin-3-ylidene)hydrazono)methyl)-2,4-dimethyl-1H-pyrrole-4-carboxylic acid (355 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (450 mg, 74%) as a red solid. LC-MS (m/z) 609 (M+1).

EXAMPLE 45

Preparation of (Z)-N-(2-aminophenyl)-6-(2-(2-((6-methoxy-2-oxoindolin-3-ylidene)methyl)-3,5-dimethyl-1H-pyrrole-4-carboxamido)ethylamino)nicotinamide

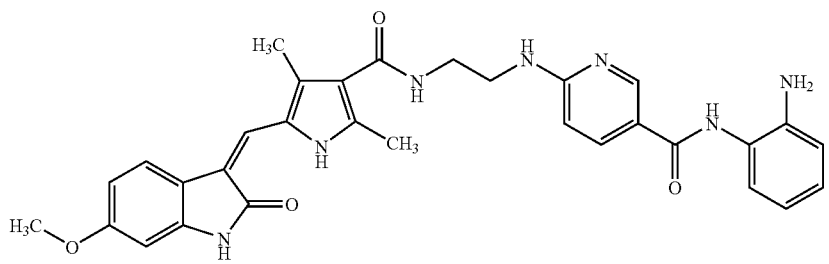

5-(6-Methoxy-2-oxo-1,2-dihydro-indol-(3Z)-ylidenemethyl)-2,4-dimethyl-1H-pyrrole-3-carboxylic acid (312 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (463 mg, 82%) as a yellow solid. LC-MS (m/z) 566 (M+1).

EXAMPLE 46

Preparation of N-(2-aminophenyl)-6-(2-(2-(((6-methoxy-2-oxoindolin-3-ylidene)hydrazono)-methyl)-3,5-dimethyl-1H-pyrrole-4-carboxamido)ethylamino)nicotinamide

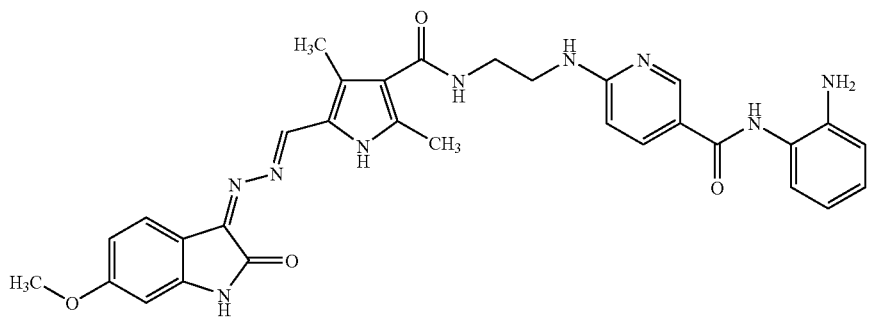

2-(((6-Methoxy-2-oxoindolin-3-ylidene)hydrazono)methyl)-2,4-dimethyl-1H-pyrrole-4-carboxylic acid (340 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (397 mg, 67%) as a red solid. LC-MS (m/z) 594 (M+1).

EXAMPLE 47

Preparation of (Z)-N-(2-aminophenyl)-6-(2-(2-((6-trifluoromethyl-2-oxoindolin-3-ylidene)methyl)-3,5-dimethyl-1H-pyrrole-4-carboxamido)ethylamino) nicotinamide

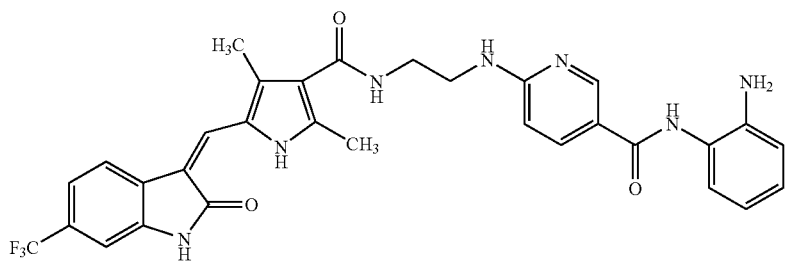

5-(6-Trifluoromethyl-2-oxo-1,2-dihydro-indol-(3Z)-ylidenemethyl)-2,4-dimethyl-1H-pyrrole-3-carboxylic acid (350 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (356 mg, 59%) as a yellow solid. LC-MS (m/z) 604 (M+1).

EXAMPLE 48

Preparation of N-(2-aminophenyl)-6-(2-(2-(((6-trifluoromethyl-2-oxoindolin-3-ylidene)-hydrazono)methyl)-3,5-dimethyl-1H-pyrrole-4-carboxamido)ethylamino)nicotinamide

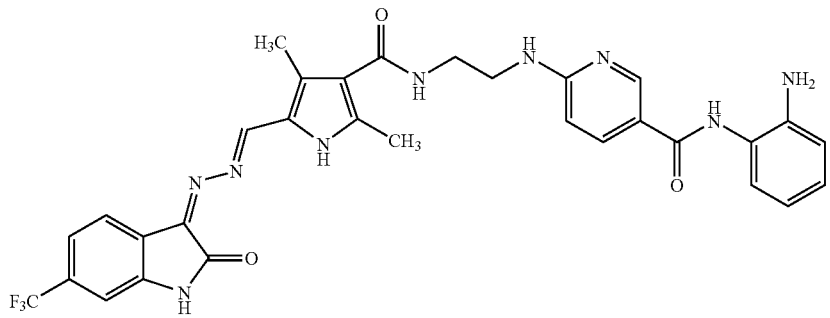

2-(((6-Trifluoromethyl-2-oxoindolin-3-ylidene)hydrazono)methyl)-2,4-dimethyl-1H-pyrrole-4-carboxylic acid (378 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(2-aminoethylamino)nicotinamide (284 mg, 1.05 mmol) were added. The mixture was stirred for 20 hours at room temperature. The mixture was diluted with 400 mL of brine. The solids were collected by vacuum filtration, washed with water and dried under vacuum to give the title compound (341 mg, 54%) as a red solid. LC-MS (m/z) 632 (M+1).

EXAMPLE 49

Preparation of N-(2-aminophenyl)-6-(6-aminohexylamino)nicotinamide

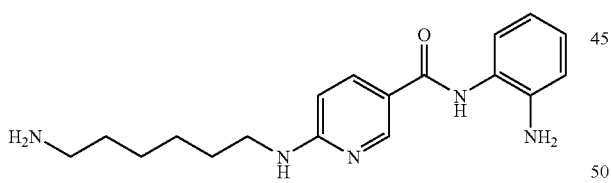

N-(2-Aminophenyl)-6-chloronicotinamide (248 mg, 1 mmol) and 1,6-diaminohexane (5.80 g, 50 mmol) were heated to 80° C. for 3 hours. The excess 1,6-diaminohexane was removed under vacuum. To the residue was added 5 ml of 0.20 M NaOH. The mixture was extracted with 100 ml of ethyl acetate. The ethyl acetate was removed under vacuum to give the title compound (219 mg, 67% yield) as a brown solid. LC-MS (m/z) 328 (M+1).

EXAMPLE 50

Preparation of (Z)-N-(2-aminophenyl)-6-(6-(2-((5-fluoro-2-oxoindolin-3-ylidene)methyl)-3,5-dimethyl-1H-pyrrole-4-carboxamido)hexylamino)nicotinamide

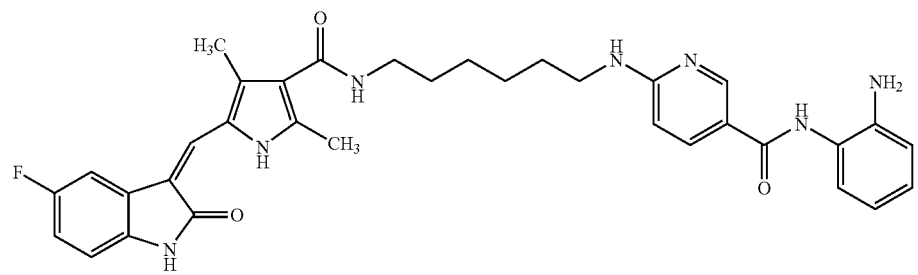

5-(5-Fuoro-2-oxo-1,2-dihydro-indol-(3Z)-ylidenemethyl)-2,4-dimethyl-1H-pyrrole-3-carboxylic acid (300 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(6-aminohexylamino)nicotinamide (343 mg, 1.05 mmol) were added. The mixture was stirred for 20 hours at room temperature. The mixture was diluted with 400 mL of brine. The solids were collected by vacuum filtration, washed with water and dried under vacuum to give the title compound (487 mg, 80%) as a yellow solid. LC-MS (m/z) 610 (M+1).

EXAMPLE 51

Preparation of N-(2-aminophenyl)-6-(6-(2-(((5-fluoro-2-oxoindolin-3-ylidene)hydrazono)-methyl)-3,5-dimethyl-1H-pyrrole-4-carboxamido)hexylamino)nicotinamide

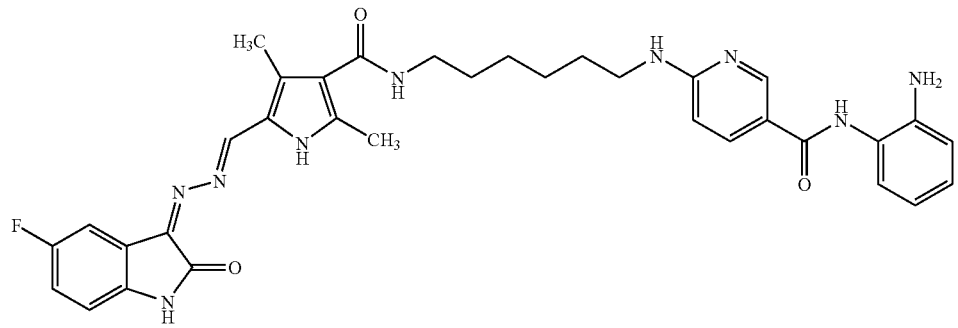

2-(((5-Fluoro-2-oxoindolin-3-ylidene)hydrazono)methyl)-2,4-dimethyl-1H-pyrrole-4-carboxylic acid (328 mg, 1 mmol) and 8 ml of DMF were stirred at room temperature while 1-Ethyl-3-(3-dimethylaminopropyl)carbodiimide hydrochloride (384 mg, 2 mmol), hydroxybenzotriazole (162 mg, 1.2 mmol), triethylamine (404 mg, 4 mmol) and N-(2-aminophenyl)-6-(6-aminohexylamino)nicotinamide (343 mg, 1.05 mmol) were added. The mixture was stirred for 20 hours at room temperature. The mixture was diluted with 400 mL of brine. The solids were collected by vacuum filtration, washed with water and dried under vacuum to give the title compound (427 mg, 67%) as a red solid. LC-MS (m/z) 638 (M+1).

EXAMPLE 52

In Vivo Inhibition of Receptor Tyrosine Kinase Activity Via Ligand-Dependent Cell Proliferation Assay by Compounds from Formula (I)

| Example (compound) | GI$_{50}$ nM (c-Kit ligand-dependent cell proliferation) | GI$_{50}$ nM (PDGF ligand-dependent cell proliferation) | GI$_{50}$ nM (VEGF ligand-dependent cell proliferation) |
| --- | --- | --- | --- |
| 3 | 126 | >1000 | <1 |
| 4 | >1000 | >1000 | 1 |
| 6 | 46 | >1000 | 9 |
| 7 | >1000 | >1000 | 387 |

-continued

| Example (compound) | GI$_{50}$ nM (c-Kit ligand-dependent cell proliferation) | GI$_{50}$ nM (PDGF ligand-dependent cell proliferation) | GI$_{50}$ nM (VEGF ligand-dependent cell proliferation) |
| --- | --- | --- | --- |
| 9 | 32 | 105 | 12 |
| 10 | >1000 | >1000 | 568 |
| 13 | 151 | >1000 | 7 |
| 14 | >1000 | >1000 | 201 |
| 16 | 105 | >1000 | 39 |
| 17 | >1000 | >1000 | 460 |
| 19 | 42 | >1000 | 81 |
| 20 | >1000 | >1000 | 330 |

Measurement of in vivo inhibition on receptor ligand-dependent cell proliferation:

PDGF dependent cell proliferation:

NIH-3T3 mouse fibroblasts cell line engineered to stably express human PDGFRβ was constructed and used to evaluate PDGF dependent cell proliferation. PDGFRβ NIH-3T3 cells were plated into 96-well plates at 5,000 per well and incubated with serum-free medium for 24 hours. Compounds and PDGF BB (50 ng/ml) were added and incubated for 72 hours in serum-free medium. The effects on proliferation were determined by addition of MTS reagent (Promega) according to the instruction, incubation for 2 hours at 37° C. in $CO_2$ incubator, and record the absorbance at 490 nm using an ELISA plate reader.

VEGF dependent cell proliferation:

HUVEC cells were plated into 96-well plates at 6,000 per well and incubated with serum-free medium for 2 hours. Compounds and VEGF 165 (50 ng/ml) were added and incubated for 72 hours in serum-free medium. The effects on proliferation were determined by addition of MTS reagent (Promega) according to the instruction, incubation for 2 hours at 37° C. in $CO_2$ incubator, and record the absorbance at 490 nm using an ELISA plate reader.

SCF dependent cell proliferation:

Mo7e cells (SCF dependent) were plated into 96-well plates at 15000 per well and incubated in 1640 medium with 10% FBS and SCF (50 ng/ml) for 24 hours. Compounds were added and incubated for 72 hours at 37° C. in $CO_2$ incubator. The effects on proliferation were determined by addition of MTS reagent (Promega) according to the instruction, incubation for 2 hours at 37° C. in $CO_2$ incubator, and record the absorbance at 490 nm using an ELISA plate reader.

EXAMPLE 53

In Vitro Inhibition of Enzyme Activities on 4 Different Receptor Tyrosine Kinases by Compounds from Formula (I)

| Example (compound) | IC$_{50}$ nM (c-Kit) | IC$_{50}$ nM (PDGFβ) | IC$_{50}$ nM (VEGFR2) | IC$_{50}$ nM (Flt3) |
|---|---|---|---|---|
| 3 | 157 | 780 | 11 | 76 |
| 4 | >1000 | >1000 | 12 | 870 |
| 6 | 76 | >1000 | 45 | 132 |
| 7 | >1000 | >1000 | 634 | 451 |
| 9 | 23 | 276 | 35 | 25 |
| 10 | >1000 | >1000 | >1000 | >1000 |
| 13 | 534 | 468 | 43 | 63 |
| 14 | >1000 | >1000 | 324 | 432 |
| 16 | 242 | >1000 | 72 | 623 |
| 17 | >1000 | >1000 | >1000 | >1000 |
| 19 | 65 | >1000 | 157 | 21 |
| 20 | >1000 | >1000 | >1000 | >1000 |

Measurement of in vitro inhibition on enzyme activity of receptor tyrosine kinase:

PDGFRα Bioassay:

This assay is used to measure in vitro kinase activity of PDGFRα in an ELISA assay.

Materials and Reagent:
1. Streptavidin coated-96-well-white plate
2. Phospho-Tyrosine Monoclonal Antibody (P-Tyr-100) (Cell Signaling)
3. HRP-labeled anti-mouse IgG (Upstate)
4. HTScan™ Tyrosine Kinase Buffer (4×)
5. DTT (1000×. 1.25 M)
6. ATP (10 mM)
7. FLT3 (Tyr589) Biotinylated Peptide Substrate (Cell Signaling)
8. PDGF Receptor α Kinase (Cell Signaling)
9. Wash Buffer: 1× PBS, 0.05% Tween-20 (PBS/T)
10. Bovine Serum Albumin (BSA)
11. Stop Buffer: 50 mM EDTA, pH 8
12. Enhanced chemiluminescence (ECL) (Amersham)

Procedure for performing the assay in 96-well plate:
1. Add 10 µl 10 mM ATP to 1.25 ml 6 µM substrate peptide. Dilute the mixture with dH$_2$0 to 2.5 ml to make 2× ATP/substrate cocktail ([ATP]=400 µM, [substrate]=3 µm).
2. Immediately transfer enzyme from −80° C. to ice. Allow enzyme to thaw on ice.
3. Microcentrifuge briefly at 4° C. to bring liquid to the bottom of the vial. Return immediately to ice.
4. Add 10 µl of DTT (1.25 M) to 2.5 ml of 4× HTScan™ Tyrosine Kinase Buffer (240 mM HEPES pH 7.5, 20 mM MgCl$_2$, 20 mM MnCl$_2$, 12 µM Na$_3$VO$_4$) to make DTT/Kinase buffer.
5. Transfer 1.25 ml of DTT/Kinase buffer to enzyme tube to make 4× reaction cocktail ([enzyme]=4 ng/µL in 4× reaction cocktail).
6. Incubate 12.5 µl of the 4× reaction cocktail with 12.5 µl/well of prediluted compound of interest (usually around 10 µM) for 5 minutes at room temperature.
7. Add 25 µl of 2× ATP/substrate cocktail to 25 µl/well pre-incubated reaction cocktail/compound. Final Assay Conditions for a 50 µl Reaction:
   60 mM HEPES pH 7.5
   5 mM MgCl$_2$
   5 mM MnCl$_2$
   3 µM Na$_3$VO$_4$
   1.25 mM DTT
   200 µM ATP
   1.5 µM peptide
   50 ng PDGF Receptor Kinase
1. Incubate reaction plate at room temperature for 30 minutes.
2. Add 50 µl/well Stop Buffer (50 mM EDTA, pH 8) to stop the reaction.
3. Transfer 25 µl of each reaction and 75 µl dH$_2$O/well to a 96-well streptavidin-coated plate and incubate at room temperature for 60 minutes.
11. Wash three times with 200 µl/well PBS/T
12. Dilute primary antibody, Phospho-Tyrosine Monoclonal Antibody (P-Tyr-100), 1:1000 in PBS/T with 1% BSA. Add 100 µl/well of primary antibody.
13. Incubate at room temperature for 60 minutes.
14. Wash three times with 200 µl/well PBS/T
15. Dilute HRP labeled anti-mouse IgG 1:500 in PBS/T with 1% BSA. Add 100 µl/well diluted antibody.
16. Incubate at room temperature for 30 minutes.
17. Wash five times with 200 µl/well PBS/T.
18. Add 100 µl/well ECL Solution.
19. Detect luminescence with appropriate Plate Reader.

VEGFR1 Bioassay

This assay is used to measure in vitro kinase activity of VEGFR1 in an ELISA assay.

Materials and Reagent:
1. Streptavidin coated, 96-well, white plate
2. Phospho-Tyrosine Monoclonal Antibody (P-Tyr-100) (Cell Signaling)
3. HRP-labeled anti-mouse IgG (Upstate)
4. HTScan™ Tyrosine Kinase Buffer (4×)
5. DTT (1000×. 1.25 M)
6. ATP (10 mM)
7. Gastrin Precursor (Tyr87) Biotinylated Peptide Substrate (Cell Signaling)
8. VEGF Receptor 1 Kinase (recombinant, human) (Cell Signaling)
9. Wash Buffer: 1× PBS, 0.05% Tween-20 (PBS/T)
10. Bovine Serum Albumin (BSA)
11. Stop Buffer: 50 mM EDTA pH 8
12. Enhanced chemiluminescence (ECL) (Amersham)

Procedure for performing the assay in 96-well plate:
1. Add 10 µl 10 mM ATP to 1.25 ml 6 µM substrate peptide. Dilute the mixture with dH$_2$0 to 2.5 ml to make 2× ATP/substrate cocktail ([ATP]=400 µM, [substrate]=3 µm).
2. Immediately transfer enzyme from −80° C. to ice. Allow enzyme to thaw on ice.
3. Microcentrifuge briefly at 4° C. to bring liquid to the bottom of the vial. Return immediately to ice.
4. Add 10 µl of DTT (1.25 M) to 2.5 ml of 4× HTScan™ Tyrosine Kinase Buffer (240 mM HEPES pH 7.5, 20 mM MgCl$_2$, 20 mM MnCl$_2$, 12 µM Na$_3$VO$_4$) to make DTT/Kinase buffer.
5. Transfer 1.25 ml of DTT/Kinase buffer to enzyme tube to make 4× reaction cocktail ([enzyme]=4 ng/µL in 4× reaction cocktail).
6. Incubate 12.5 µl of the 4× reaction cocktail with 12.5 µl/well of prediluted compound of interest (usually around 10 µM) for 5 minutes at room temperature.
7. Add 25 µl of 2× ATP/substrate cocktail to 25 µl/well pre-incubated reaction cocktail/compound. Final Assay Conditions for a 50 µl Reaction:
   60 mM HEPES pH 7.5
   5 mM MgCl$_2$
   5 mM MnCl$_2$
   3 µM Na$_3$VO$_4$ 1.25 mM DTT
200 μM ATP
1.5 μM peptide
100 ng VEGFR1 Kinase
8. Incubate reaction plate at room temperature for 30 minutes.
9. Add 50 μl/well Stop Buffer (50 mM EDTA, pH 8) to stop the reaction.
10. Transfer 25 μl of each reaction and 75 μl dH₂O/well to a 96-well streptavidincoated plate and incubate at room temperature for 60 minutes.
11. Wash three times with 200 μl/well PBS/T
12. Dilute primary antibody, Phospho-Tyrosine Monoclonal Antibody (P-Tyr-100), 1:1000 in PBS/T with 1% BSA. Add 100 μl/well of primary antibody.
13. Incubate at room temperature for 60 minutes.
14. Wash three times with 200 μl/well PBS/T
15. Dilute HRP labeled anti-mouse IgG 1:500 in PBS/T with 1% BSA. Add 100 μl/well diluted antibody.
16. Incubate at room temperature for 30 minutes.
17. Wash five times with 200 μl/well PBS/T.
18. Add 100 μl/well ECL Solution.
19. Detect luminescence with appropriate Plate Reader.

c-KIT Bioassay

This assay is used to measure in vitro kinase activity of c-KIT in an ELISA assay.
Materials and Reagent:
1. Streptavidin coated, 96-well, white plate
2. Phospho-Tyrosine Monoclonal Antibody (P-Tyr-100) (Cell Signaling)
3. HRP-labeled anti-mouse IgG (Upstate)
4. HTScan™ Tyrosine Kinase Buffer (4×)
5. DTT (1000×. 1.25 M)
6. ATP (10 mM)
7. KDR (Tyr996) Biotinylated Peptide Substrate (Cell Signaling)
8. c-KIT Kinase (recombinant, human) (Cell Signaling)
9. Wash Buffer: 1× PBS, 0.05% Tween-20 (PBS/T)
10. Bovine Serum Albumin (BSA)
11. Stop Buffer: 50 mM EDTA pH 8
12. Enhanced chemiluminescence (ECL) (Amersham)
Procedure for performing the assay in 96-well plate:
1. Add 10 μl 10 mM ATP to 1.25 ml 6 μM substrate peptide. Dilute the mixture with dH₂0 to 2.5 ml to make 2× ATP/substrate cocktail ([ATP]=40 μM, [substrate]=3 μm).
2. Immediately transfer enzyme from −80° C. to ice. Allow enzyme to thaw on ice.
3. Microcentrifuge briefly at 4° C. to bring liquid to the bottom of the vial. Return immediately to ice.
4. Add 10 μl of DTT (1.25 M) to 2.5 ml of 4× HTScan™ Tyrosine Kinase Buffer (240 mM HEPES pH 7.5, 20 mM MgCl₂, 20 mM MnCl₂, 12 μM Na₃VO₄) to make DTT/Kinase buffer.
5. Transfer 1.25 ml of DTT/Kinase buffer to enzyme tube to make 4× reaction cocktail ([enzyme]=4 ng/μL in 4× reaction cocktail).
6. Incubate 12.5 μl of the 4× reaction cocktail with 12.5 μl/well of prediluted compound of interest (usually around 10 μM) for 5 minutes at room temperature.
7. Add 25 μl of 2× ATP/substrate cocktail to 25 μl/well preincubated reaction cocktail/compound. Final Assay Conditions for a 50 μl Reaction:
60 mM HEPES pH 7.5
5 mM MgCl₂
5 mM MnCl₂
3 μM Na₃VO₄
1.25 mM DTT
20 μM ATP
1.5 μM peptide
100 ng c-KIT Kinase
8. Incubate reaction plate at room temperature for 30 minutes.
9. Add 50 μl/well Stop Buffer (50 mM EDTA, pH 8) to stop the reaction.
10. Transfer 25 μl of each reaction and 75 μl dH₂O/well to a 96-well streptavidincoated plate and incubate at room temperature for 60 minutes.
11. Wash three times with 200 μl/well PBS/T
12. Dilute primary antibody, Phospho-Tyrosine Monoclonal Antibody (P-Tyr-100), 1:1000 in PBS/T with 1% BSA. Add 100 μl/well of primary antibody.
13. Incubate at room temperature for 60 minutes.
14. Wash three times with 200 μl/well PBS/T
15. Dilute HRP labeled anti-mouse IgG 1:500 in PBS/T with 1% BSA. Add 100 μl/well diluted antibody.
16. Incubate at room temperature for 30 minutes.
17. Wash five times with 200 μl/well PBS/T.
18. Add 100 μl/well ECL Solution.
19. Detect luminescence with appropriate Plate Reader.

Flt3 Bioassay

This assay is used to measure in vitro kinase activity of Flt3 in an ELISA assay.
Materials and Reagent:
1. Streptavidin coated, 96-well, white plate
2. Phospho-Tyrosine Monoclonal Antibody (P-Tyr-100) (Cell Signaling)
3. HRP-labeled anti-mouse IgG (Upstate)
4. HTScan™ Tyrosine Kinase Buffer (4×)
5. DTT (1000×. 1.25 M)
6. ATP (10 mM)
7. KDR (Tyr996) Biotinylated Peptide Substrate (Cell Signaling)
8. Flt3 Kinase (recombinant, human) (Cell Signaling)
9. Wash Buffer: 1× PBS, 0.05% Tween-20 (PBS/T)
10. Bovine Serum Albumin (BSA)
11. Stop Buffer: 50 mM EDTA pH 8
12. Enhanced chemiluminescence (ECL) (Amersham)
Procedure for performing the assay in 96-well plate:
1. Add 10 μl 10 mM ATP to 1.25 ml 6 μM substrate peptide. Dilute the mixture with dH₂0 to 2.5 ml to make 2× ATP/substrate cocktail ([ATP]=400 μM, [substrate]=3 μm).
2. Immediately transfer enzyme from −80° C. to ice. Allow enzyme to thaw on ice.
3. Microcentrifuge briefly at 4° C. to bring liquid to the bottom of the vial. Return immediately to ice.
4. Add 10 μl of DTT (1.25 M) to 2.5 ml of 4× HTScan™ Tyrosine Kinase Buffer (240 mM HEPES pH 7.5, 20 mM MgCl₂, 20 mM MnCl₂, 12 μM Na₃VO₄) to make DTT/Kinase buffer.
5. Transfer 1.25 ml of DTT/Kinase buffer to enzyme tube to make 4× reaction cocktail ([enzyme]=4 ng/μL in 4× reaction cocktail).
6. Incubate 12.5 μl of the 4× reaction cocktail with 12.5 μl/well of prediluted compound of interest (usually around 10 μM) for 5 minutes at room temperature.
7. Add 25 μl of 2× ATP/substrate cocktail to 25 μl/well preincubated reaction cocktail/compound. Final Assay Conditions for a 50 μl Reaction:
60 mM HEPES pH 7.5
5 mM MgCl₂
5 mM MnCl₂
3 μM Na₃VO₄
1.25 mM DTT
200 μM ATP
1.5 μM peptide
10 units Flt3 Kinase 8. Incubate reaction plate at room temperature for 30 minutes.
9. Add 50 µl/well Stop Buffer (50 mM EDTA, pH 8) to stop the reaction.
10. Transfer 50 µl of each reaction and 50 µl dH$_2$O/well to a 96-well streptavidincoated plate and incubate at room temperature for 60 minutes.
11. Wash three times with 200 µl/well PBS/T
12. Dilute primary antibody, Phospho-Tyrosine Monoclonal Antibody (P-Tyr-100), 1:1000 in PBS/T with 1% BSA. Add 100 µl/well of primary antibody.
13. Incubate at room temperature for 60 minutes.
14. Wash three times with 200 µl/well PBS/T
15. Dilute HRP labeled anti-mouse IgG 1:500 in PBS/T with 1% BSA. Add 100 µl/well diluted antibody.
16. Incubate at room temperature for 30 minutes.
17. Wash five times with 200 µl/well PBS/T.
18. Add 100 µl/well ECL Solution.
19. Detect luminescence with appropriate Plate Reader.

The assays to measure enzyme activity of all other receptor tyrosine kinases are essentially identical to that as exemplified in the case of VEGF, PDGF, c-Kit or Flt3 receptor tyrosine kinase assay except specific receptor tyrosine kinase reagent may be used in a given receptor tyrosine kinase context.

EXAMPLE 54

In Vitro Inhibition of Total HDAC Enzyme Activity and In Vivo Inhibition of HDAC Subtype Activity by Compounds from Formula (I)

Measurement of in vitro inhibition of total HDAC enzyme activity:

The in vitro inhibition of total HDAC enzyme was determined by HDAC Fluorimetric Assay/Drug Discovery Kit (BIOMOL) according to manufacture's instruction.

1. Add Assay buffer, diluted trichostatin A or test inhibitor to appropriate wells of the microtiter plate. Following table lists examples of various assay types and the additions required for each test.

| Sample | Assay Buffer | HeLa Extract (Dilution) | Inhibitor (5x) | *Fluor de Lys* ™ Substrate (2x) |
|---|---|---|---|---|
| Blank (No Enzyme) | 25 µl | 0 | 0 | 25 µl |
| Control | 10 µl | 15 µl | 0 | 25 µl |
| Trichostatin A | 0 | 15 µl | 10 µl | 25 µl |
| Test Sample | 0 | 15 µl | 10 µl | 25 µl |

2. Add diluted HeLa extract or other HDAC sample to all wells except those that are to be "No Enzyme Controls" (Blank).
3. Allow diluted Fluor de Lys™ Substrate and the samples in the microtiter plate to equilibrate to assay temperature (25° C.).
4. Initiate HDAC reactions by adding diluted substrate (25 µl) to each well and mixing thoroughly.
5. Allow HDAC reactions to proceed for desired length of time and then stop them by addition of Fluor de Lys™ Developer (50 µl). Incubate plate at room temperature (25° C.) for 10-15 min.

| Example (compound) | % inhibition of total HDAC enzyme activity at 30 µM | Class I HDAC (P21 reporter assay) EC$_{50}$ µM | | HDAC3 (GDF11 reporter assay) EC$_{50}$ µM | | HDAC4/5 (MEF2 reporter assay) EC$_{50}$ µM | | HDAC7 (Nur77 reporter assay) EC$_{50}$ µM | |
|---|---|---|---|---|---|---|---|---|---|
| | | EC$_{50}$ µM | % Max Resp of CS055 at 3 µM | EC$_{50}$ µM | % Max Resp of CS055 at 3 µM | EC$_{50}$ µM | % Max Resp of CS055 at 3 µM | EC$_{50}$ µM | % Max Resp of CS055 at 3 µM |
| CS055 | 46.2 | 3.5 | 100.0 | 3.2 | 100.0 | 15.1 | 100.0 | 6.8 | 100.0 |
| SAHA | 95.7 | 0.5 | 304.1 | 0.8 | 317.9 | 1.2 | 427.3 | 3.0 | 514.9 |
| 3 | 9.20 | 2.3 | 131.7 | 1.9 | 106.2 | 2.2 | 83.2 | 2.9 | 113.5 |
| 4 | 6.90 | nd | 3.3 | nd | 2.4 | nd | 4.9 | nd | 3.9 |
| 6 | 12.50 | 2.5 | 74.6 | 1.0 | 75.6 | 1.0 | 44.2 | 2.5 | 88.1 |
| 7 | 7.80 | nd | 6.2 | nd | 6.3 | nd | 2.6 | nd | 12.4 |
| 9 | 6.30 | 13.4 | 89.1 | 15.5 | 81.4 | 20.0 | 53.6 | 13.2 | 88.7 |
| 10 | 6.10 | nd | 7.3 | nd | 8.3 | nd | 12.8 | nd | 13.2 |
| 13 | −2.60 | nd | 2.1 | nd | 1.8 | nd | 0.5 | nd | 6.4 |
| 14 | 1.00 | nd | 2.1 | nd | 2.0 | nd | 2.4 | nd | 4.5 |
| 16 | 6.70 | nd | 2.5 | nd | 1.8 | nd | −0.2 | nd | 6.5 |
| 17 | 4.00 | nd | 3.4 | nd | 3.8 | nd | 10.8 | nd | 3.5 |
| 19 | 7.30 | nd | 2.3 | nd | 2.0 | nd | 1.9 | nd | 6.0 |
| 20 | 3.50 | nd | 2.8 | nd | 4.1 | nd | 16.3 | nd | 1.0 | nd*: not determined
CS055: Chidamide is a HDACi currently in clinic development against cancers with good efficacy and toxicity profile from Chipscreen Biosciences 6. Read samples in a microtiter-plate reading fluorimeter capable of excitation at a wavelength in the range 350-380 nm and detection of emitted light in the range 440-460 nm.

Measurement of in vivo inhibition of HDAC subtype activity:

HDAC subtype selectivity inhibition assay of tested compounds was carried out by several reporter gene assays experiments. Briefly, HeLa cells were seeded in 96-well plates the day before transfection to give a confluence of 50-80%. Cells were transfected with one of reporter gene plasmid containing a promoter sequence or response element upstream of a luciferase gene construct using FuGene6 transfection reagent according to the manufacturer's instruction (Roche). The promoters or response elements including p21-promoter, gdf11-promoter, MEF-binding element (MEF2), Nur77-promoter were fused upstream to the luciferase gene reporter construct. For normalizing the transfection efficiency, a GFP expression plasmid was cotransfected. Cells were allowed to express protein for 24 hours followed by addition of individual compounds or the vehicle (DMSO). 24 hours later the cells were harvested, and the luciferase assay and GFP assay were performed using corresponding assay kits according to the manufacturer's instructions (Promega).

EXAMPLE 55

In Vivo Anti-Proliferation by Compounds from Formula (I)

Human Cell lines are listed below:

| HL-60: | Acute promyelocytic leukemia |
| Hut-78: | Cutaneous T cell lymphoma |
| Raji: | Burkitt's lymphoma |
| Jurkat: | T cell leukemia |
| U937: | Histiocytic lymphoma |
| Ramos: | Burkitt's lymphoma |
| A549: | Non small cell lung carcinoma |
| HeLa: | Cervix adenocarcinoma |
| Bel-7402: | Hepatocellular carcinoma |
| MCF-7: | Mammary gland adenocarcinoma |
| MDA-MB-231: | Mammary gland adenocarcinoma |
| HCT-8: | Ileocecal colorectal adenocarcinoma |

| Example (compound) | $GI_{50}$ μM in HL60 | $GI_{50}$ μM in Hut-78 | $GI_{50}$ μM in Raji | $GI_{50}$ μM in Jurkat | $GI_{50}$ μM in U937 | $GI_{50}$ μM in Ramos | $GI_{50}$ μM in A549 | $GI_{50}$ μM in HeLa | $GI_{50}$ μM in Bel-7402 | $GI_{50}$ μM in MCF7 | $GI_{50}$ μM in MDA-MB-231 | $GI_{50}$ μM in HCT-8 |
|---|---|---|---|---|---|---|---|---|---|---|---|---|
| 3 | 4.15 | 1.77 | 3.45 | >60 | >60 | >60 | >60 | >60 | >60 | >60 | >60 | >60 |
| 4 | >60 | >60 | >60 | >60 | >60 | >60 | >60 | >60 | >60 | >60 | >60 | >60 |
| 6 | >60 | >60 | 3.45 | >60 | >60 | >60 | >60 | >60 | >60 | >60 | >60 | >60 |
| 7 | 7.91 | >60 | >60 | >60 | >60 | >60 | >60 | >60 | >60 | >60 | >60 | >60 |
| 9 | 1.27 | 1.67 | >60 | >60 | >60 | >60 | >60 | >60 | >60 | >60 | >60 | >60 |
| 10 | 6.28 | >60 | >60 | >60 | >60 | >60 | >60 | >60 | >60 | >60 | >60 | >60 |
| 13 | >60 | >60 | >60 | >60 | >60 | >60 | >60 | >60 | >60 | >60 | >60 | >60 |
| 14 | >60 | >60 | >60 | >60 | >60 | >60 | >60 | >60 | >60 | >60 | >60 | >60 |
| 16 | >60 | >60 | >60 | >60 | >60 | >60 | >60 | >60 | >60 | >60 | >60 | >60 |
| 17 | >60 | >60 | >60 | >60 | >60 | >60 | >60 | >60 | >60 | >60 | >60 | >60 |
| 19 | >60 | >60 | >60 | >60 | >60 | >60 | >60 | >60 | >60 | >60 | >60 | >60 |
| 20 | >60 | >60 | >60 | >60 | >60 | >60 | >60 | >60 | >60 | >60 | >60 | >60 |
| CS055 | 1.00 | 1.69 | 9.29 | 3.79 | 2.50 | >60 | 13.75 | 21.29 | 28.06 | >60 | 36.15 | >60 |
| Sorafinib | 1.28 | 12.54 | 4.15 | 16.91 | 4.06 | 1.51 | 13.75 | 30.77 | 9.73 | 9.51 | 4.25 | 5.35 |
| Sutent | 1.73 | 4.06 | 5.47 | 7.05 | 8.28 | 11.97 | 14.73 | 9.29 | 13.13 | 7.55 | 4.66 | 12.25 |

Note:
Chidamide is a HDAC inhibitor currently in clinic development against cancers with preference against class I HDAC enzyme; Suten and Sorafinib are two marketed RTK and Ser/Thr kinase inhibitors with broad activity against many different receptor tyrosine or ser/thr kinases Measurement of in vivo cell proliferation:

Tumor cells were trypsinized and plated into 96-well plates at 3,000 per well and incubated in complete medium with 10% FBS for 24 hours. Compounds were added over a final concentration range of 100 μmol/L to 100 nmol/L in 0.1% DMSO and incubated for 72 hours in complete medium. The effects on proliferation were determined by addition of MTS reagent (Promega) according to the instruction, incubation for 2 hours at 37° C. in $CO_2$ incubator, and record the absorbance at 490 nm using an ELISA plate reader.

What is claimed is:
1. An isolated compound of formula I:

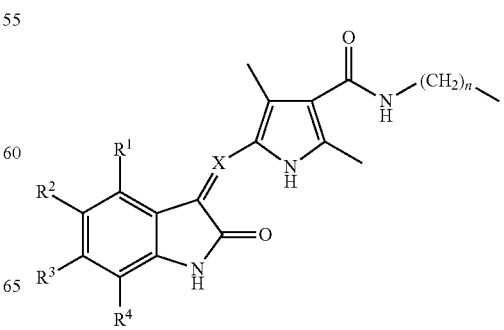

(I)

-continued or its stereoisomer, enantiomer, diastereomer, or a pharmaceutically acceptable salt thereof, wherein
X is =CH— or =N—N=CH—;
R$^1$, R$^2$, R$^3$ and R$^4$ are independently hydrogen, halo, alkyl, alkoxy, nitro or trifluoromethyl;
R$^5$, R$^6$, R$^7$ and R$^8$ are independently hydrogen, halo, alkyl, alkoxy or trifluoromethyl;
n is an integer ranging from 2 to 6.

2. A compound of claim 1, wherein
X is =CH—;
R$^1$, R$^2$, R$^3$ and R$^4$ are independently hydrogen, halo, alkyl, alkoxy, nitro or trifluoromethyl;
R$^5$, R$^6$, R$^7$ and R$^8$ are independently hydrogen, halo, alkyl, alkoxy or trifluoromethyl;
n is an integer ranging from 2 to 4.

3. A compound of claim 1, wherein
X is =CH—;
R$^1$, R$^2$, R$^3$ and R$^4$ are independently hydrogen, halo, alkyl, alkoxy, nitro or trifluoromethyl;
R$^5$, R$^6$, R$^7$ and R$^8$ are independently H or F;
n is an integer ranging from 2 to 4.

4. A compound of claim 1, wherein
X is =N—N=CH—;
R$^1$, R$^2$, R$^3$ and R$^4$ are independently hydrogen, halo, alkyl, alkoxy, nitro or trifluoromethyl;
R$^5$, R$^6$, R$^7$ and R$^8$ are independently hydrogen, halo, alkyl, alkoxy or trifluoromethyl;
n is an integer ranging from 2 to 4.

5. A compound of claim 1, wherein
X is =N—N=CH—;
R$^1$, R$^2$, R$^3$ and R$^4$ are independently hydrogen, halo, alkyl, alkoxy, nitro or trifluoromethyl;
R$^5$, R$^6$, R$^7$ and R$^8$ are independently H or F;
n is an integer ranging from 2 to 4.

6. A process for the preparation of a compound of formula I wherein
X is =CH— or =N—N=CH—;
R$^1$, R$^2$, R$^3$ and R$^4$ are independently hydrogen, halo, alkyl, alkoxy, nitro or trifluoromethyl;
R$^5$, R$^6$, R$^7$ and R$^8$ are independently hydrogen, halo, alkyl, alkoxy or trifluoromethyl;
n is an integer ranging from 2 to 6;
a stereoisomer, enantiomer, diastereomer, or pharmaceutically acceptable salt thereof comprising the steps of:

(a) condensing 6-chloronicotinic acid with compound 1 to give compound 2;

(b) condensing compound 2 with compound 3 to give compound 4;

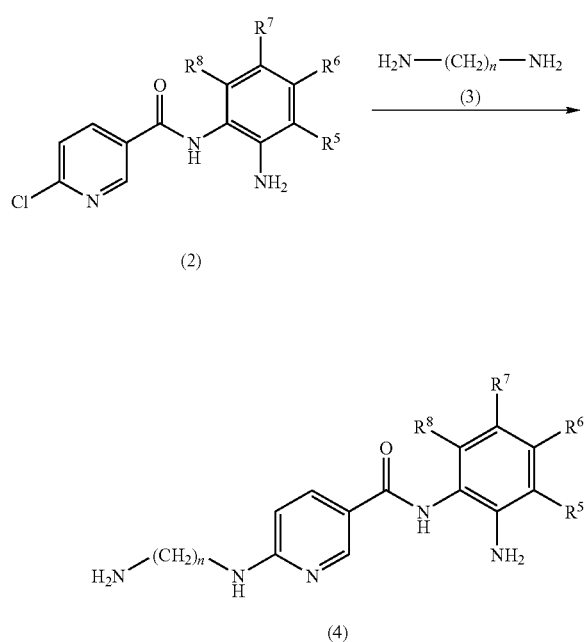

(c) condensing compound 4 with compound 5 to give compound 6;

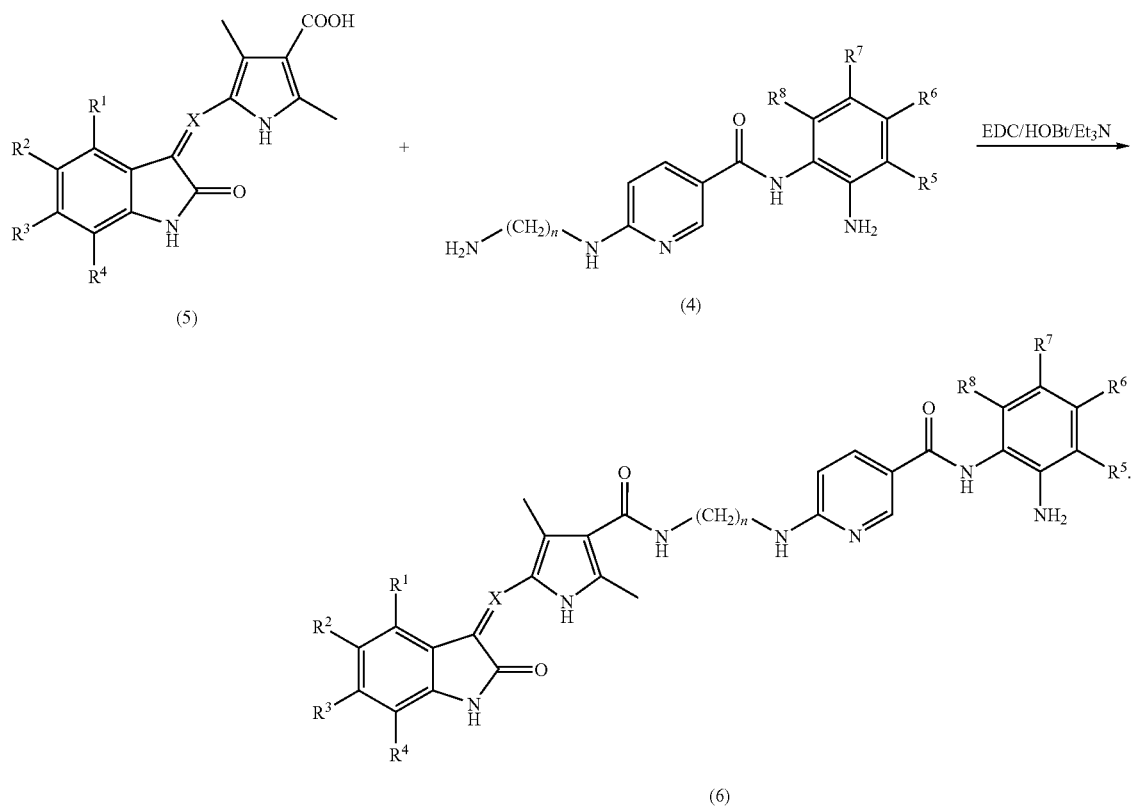

7. The process of claim 6, wherein the condensation reactions of steps (a) and (c) are conducted by using a peptide condensing agent.

8. The process of claim 7, wherein said peptide condensing agent is 1-Ethyl-3-(3-dimethyl-aminopropyl)carbodiimide, dicyclohexylcarbodiimide, or N,N'-carbonyldiimidazole.

9. A pharmaceutical composition comprising an effective amount of a compound according to claim 1 or its pharmaceutically acceptable salt and at least one pharmaceutically acceptable excipient, carrier or diluent.

10. The pharmaceutical composition according to claim 9 in unit dosage form comprising from about 0.0001 to about 200 mg of said compound.

11. A pharmaceutical composition according to claim 9 for administration by an oral, nasal, transdermal, pulmonary, or parenteral route.

12. A method of treatment of a disease associated with abnormal protein kinase activity and/or abnormal histone deacetylase activity selected from the group consisting of Acute promyelocytic leukemia;
Cutaneous T cell lymphoma;
Burkitt's lymphoma;
T cell leukemia;
Histiocytic lymphoma;
Burkitt's lymphoma;
Non small cell lung carcinoma;
Cervix adenocarcinoma;
Hepatocellular carcinoma;
Mammary gland adenocarcinoma;
Mammary gland adenocarcinoma; and
Ileocecal colorectal adenocarcinoma comprising administering to a subject in need thereof an effective amount of an isolated compound of formula I:

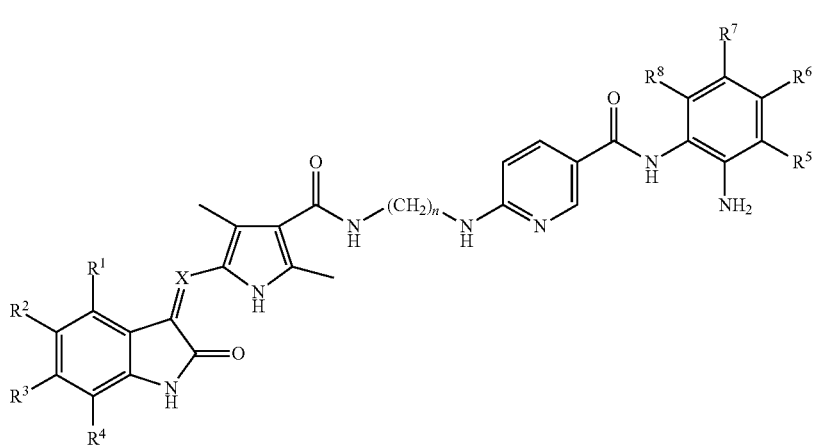
or its stereoisomer, enantiomer, diastereomer, or a pharmaceutically acceptable salt thereof, wherein
X is =CH— or =N—N=CH—;
$R^1$, $R^2$, $R^3$ and $R^4$ are independently hydrogen, halo, alkyl, alkoxy, nitro or trifluoromethyl;
$R^5$, $R^6$, $R^7$ and $R^8$ are independently hydrogen, halo, alkyl, alkoxy or trifluoromethyl;
n is an integer ranging from 2 to 6.
* * * * *